United States Patent
Tamir et al.

(10) Patent No.: US 11,602,530 B2
(45) Date of Patent: Mar. 14, 2023

(54) CRM1 INHIBITORS FOR TREATING EPILEPSY

(71) Applicant: Biogen MA Inc., Cambridge, MA (US)

(72) Inventors: Sharon Tamir, Newton, MA (US); Margaret Lee, Middleton, MA (US); Marc De Ryck, Lier (BE); Rafal M. Kaminski, Waterloo (BE); Karine Leclercq, Gosselies (BE); Benoit Kenda, Louvain La Neuve (BE)

(73) Assignee: BIOGEN MA INC., Cambridge, MA (US)

(*) Notice: Subject to any disclaimer, the term of this patent is extended or adjusted under 35 U.S.C. 154(b) by 130 days.

(21) Appl. No.: 16/463,693

(22) PCT Filed: Nov. 28, 2017

(86) PCT No.: PCT/US2017/063439
§ 371 (c)(1),
(2) Date: May 23, 2019

(87) PCT Pub. No.: WO2018/098472
PCT Pub. Date: May 31, 2018

(65) Prior Publication Data
US 2019/0374527 A1    Dec. 12, 2019

Related U.S. Application Data

(60) Provisional application No. 62/426,957, filed on Nov. 28, 2016.

(51) Int. Cl.
*A61K 31/4439* (2006.01)
*A61P 25/08* (2006.01)
(Continued)

(52) U.S. Cl.
CPC ...... *A61K 31/4439* (2013.01); *A61K 31/4196* (2013.01); *A61K 31/497* (2013.01); *A61K 31/5377* (2013.01); *A61P 25/08* (2018.01)

(58) Field of Classification Search
CPC ............ A61K 31/4196; A61K 31/4439; A61K 31/454; A61K 31/497; A61K 31/5377
(Continued)

(56) References Cited

U.S. PATENT DOCUMENTS 5,153,201 A    10/1992  Aono et al.
5,817,677 A    10/1998  Linz et al.
(Continued)

FOREIGN PATENT DOCUMENTS

CN    101309912 A    11/2008
CN    101466687 A    6/2009
(Continued)

OTHER PUBLICATIONS

Ono, Tomonori etal (Adv Exp Med Biol. Author manuscript; available in PMC Jun. 1, 20199. Published in final edited form as:Adv Exp Med Biol. 2012; 724: 99-113. doi: 10.1007/978-1-4614-0653-2_8).*
(Continued)

*Primary Examiner* — San Ming R Hui
(74) *Attorney, Agent, or Firm* — Rothwell, Figg, Ernst & Manbeck, P.C.

(57)    ABSTRACT

The invention generally relates to the use of nuclear transport modulators, e.g., CRM1 inhibitors, of Formula (I) for treating epilepsy in a subject. Subjects can have unprovoked seizures without prior warning that affect one or both hemispheres of the brain. The disclosed methods can reduce the severity and occurrence of these unprovoked epileptic seizures and can result in resolution of epilepsy. The method
(Continued)

comprises administering to the subject an effective amount of a compound represented by Formula (I) or a pharmaceutically acceptable salt thereof.

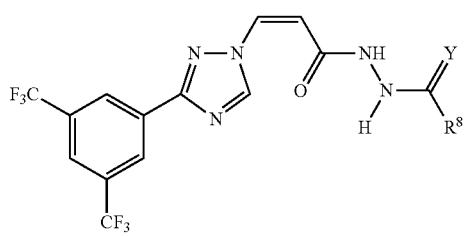

3 Claims, 4 Drawing Sheets

(51) Int. Cl.
*A61K 31/4196* (2006.01)
*A61K 31/497* (2006.01)
*A61K 31/5377* (2006.01)

(58) Field of Classification Search
USPC .................................................. 514/255.05
See application file for complete search history.

(56) References Cited

U.S. PATENT DOCUMENTS

| | | | |
|---|---|---|---|
| 6,462,049 | B1 | 10/2002 | Ogura et al. |
| 7,342,115 | B2 | 3/2008 | Hutchison et al. |
| 7,667,041 | B2 | 2/2010 | Kimura et al. |
| 7,795,457 | B2 | 9/2010 | Fu et al. |
| 7,858,621 | B2 | 12/2010 | Kim et al. |
| 7,902,367 | B2 | 3/2011 | Nomura et al. |
| 8,273,738 | B2 | 9/2012 | Osakada et al. |
| 8,299,102 | B2 | 10/2012 | Strobel et al. |
| 8,304,438 | B2 | 11/2012 | Strobel et al. |
| 8,513,230 | B2 | 8/2013 | Shacham et al. |
| 8,598,168 | B2 | 12/2013 | Moradei et al. |
| 8,999,996 | B2 | 4/2015 | Sandanayaka et al. |
| 9,079,865 | B2 * | 7/2015 | Sandanayaka ......... A61K 31/55 |
| 9,096,543 | B2 | 8/2015 | Sandanayaka et al. |
| 9,206,158 | B2 * | 12/2015 | Sandanayaka .......... A61P 35/00 |
| 9,266,843 | B2 | 2/2016 | Sandanayaka et al. |
| 9,303,000 | B2 | 4/2016 | Sandanayaka et al. |
| 9,428,490 | B2 | 8/2016 | Sandanayaka et al. |
| 9,550,757 | B2 | 1/2017 | Shacham et al. |
| 9,585,874 | B2 | 3/2017 | Sandanayaka et al. |
| 9,714,226 | B2 | 7/2017 | Sandanayaka et al. |
| 9,738,624 | B2 | 8/2017 | Baloglu et al. |
| 9,828,373 | B2 | 11/2017 | Liu et al. |
| 9,861,614 | B2 | 1/2018 | Sandanayaka et al. |
| 10,058,535 | B2 | 8/2018 | Sandanayaka et al. |
| 10,173,987 | B2 * | 1/2019 | Sandanayaka .......... A61P 27/00 |
| 10,202,366 | B2 | 2/2019 | Rashal et al. |
| 10,335,393 | B2 | 7/2019 | Sandanayaka et al. |
| 10,407,405 | B2 | 9/2019 | Shechter et al. |
| 10,544,108 | B2 * | 1/2020 | Sandanayaka .......... A61P 25/28 |
| 10,617,677 | B2 | 4/2020 | Sandanayaka et al. |
| 10,722,497 | B2 | 7/2020 | Sandanayaka et al. |
| 10,925,859 | B2 | 2/2021 | Sandanayaka et al. |
| 2003/0018025 | A1 | 1/2003 | Thurkauf et al. |
| 2009/0221586 | A1 | 9/2009 | Okada et al. |
| 2009/0298896 | A1 | 12/2009 | Sakuma et al. |
| 2010/0016272 | A1 | 1/2010 | Strobel et al. |
| 2010/0056569 | A1 | 3/2010 | Nan et al. |
| 2011/0009374 | A1 | 1/2011 | Keller |
| 2011/0275607 | A1 | 11/2011 | Shacham et al. |
| 2012/0258986 | A1 | 10/2012 | Sandanayaka et al. |
| 2013/0317031 | A1 | 11/2013 | Sandanayaka et al. |
| 2014/0155370 | A1 | 6/2014 | Shacham et al. |
| 2014/0235653 | A1 | 8/2014 | Sandanayaka et al. |
| 2014/0364408 | A1 | 12/2014 | Sandanayaka et al. |
| 2015/0018332 | A1 | 1/2015 | Sandanayaka et al. |
| 2015/0111893 | A1 | 4/2015 | Sandanayaka et al. |
| 2015/0274698 | A1 * | 10/2015 | Sandanayaka ....... C07D 409/12 514/340 |
| 2016/0145246 | A1 | 5/2016 | Sandanayaka et al. |
| 2016/0152596 | A1 | 6/2016 | Baloglu et al. |
| 2016/0258931 | A1 | 9/2016 | Silva et al. |
| 2016/0304500 | A1 | 10/2016 | Rashal et al. |
| 2017/0137430 | A1 | 5/2017 | Sandanayaka et al. |
| 2017/0319551 | A1 | 11/2017 | Sandanayaka et al. |
| 2018/0155317 | A1 | 6/2018 | Baloglu et al. |
| 2019/0008833 | A1 * | 1/2019 | Sandanayaka .......... A61P 35/00 |
| 2019/0016690 | A1 | 1/2019 | Baloglu |
| 2019/0023693 | A1 | 1/2019 | Chennuru et al. |
| 2019/0160063 | A1 | 5/2019 | Baloglu |

FOREIGN PATENT DOCUMENTS

| | | |
|---|---|---|
| CN | 103002742 A | 3/2013 |
| CN | 103874690 B | 7/2016 |
| EP | 0069513 A2 | 1/1983 |
| EP | 1 939 180 A1 | 7/2008 |
| EP | 1992618 A1 | 11/2008 |
| EP | 2003118 A1 | 12/2008 |
| EP | 2 090 570 A1 | 8/2009 |
| JP | S5841875 A | 3/1983 |
| JP | S62103065 A | 5/1987 |
| JP | H04211089 A | 8/1992 |
| JP | H07118237 A | 5/1995 |
| JP | H11263764 A | 9/1999 |
| JP | 2003/342262 A | 12/2003 |
| JP | 2004509941 A | 4/2004 |
| JP | 2004168768 A | 6/2004 |
| JP | 2005-508905 A | 4/2005 |
| JP | 2005-255683 A | 9/2005 |
| JP | 2006-504761 A | 2/2006 |
| JP | 2009-203238 A | 9/2009 |
| JP | 2009-536615 A | 10/2009 |
| JP | 2009-544696 A | 12/2009 |
| JP | 2010-513341 A | 4/2010 |
| JP | 2010-519337 A | 6/2010 |
| JP | 2015-516434 A | 6/2015 |
| JP | 2018-012715 A | 1/2018 |
| KR | 20050062645 A | 6/2005 |
| WO | WO-96/16040 A1 | 5/1996 |
| WO | WO-97/15567 A1 | 5/1997 |
| WO | WO-97/37996 A1 | 10/1997 |
| WO | WO-97/48696 A1 | 12/1997 |
| WO | WO-98/25893 A1 | 6/1998 |
| WO | WO-99/50264 A1 | 10/1999 |
| WO | WO-01/62756 A1 | 8/2001 |
| WO | WO-02/26696 A1 | 4/2002 |
| WO | WO-2003/024448 A2 | 3/2003 |
| WO | WO-2004/039365 A1 | 5/2004 |
| WO | WO-2004/039764 A1 | 5/2004 |
| WO | WO-2004/043925 A2 | 5/2004 |
| WO | WO-2004/043951 A1 | 5/2004 |
| WO | WO-2004/076418 A1 | 9/2004 |
| WO | WO-2005/115990 A1 | 12/2005 |
| WO | WO-2006/016637 A1 | 2/2006 |
| WO | WO-2006/019020 A1 | 2/2006 |
| WO | WO-2006/088246 A1 | 8/2006 |
| WO | WO-2007/102580 A1 | 9/2007 |
| WO | WO-2007/147336 A1 | 12/2007 |
| WO | WO-2008/029825 A1 | 3/2008 |
| WO | WO-2008/074413 A2 | 6/2008 |
| WO | WO-2011/069039 A1 | 6/2011 |
| WO | WO-2011/109799 A1 | 9/2011 |
| WO | WO-2012/099807 A1 | 7/2012 |
| WO | WO-2013/019548 A1 | 2/2013 |
| WO | WO-2013/019561 A1 | 2/2013 |
| WO | WO-2013/020024 A2 | 2/2013 |
| WO | WO-2013/170068 A2 | 11/2013 |
| WO | WO-2014/144772 A1 | 9/2014 |

(56) References Cited

FOREIGN PATENT DOCUMENTS

| WO | WO-2014/152263 A1 | 9/2014 |
|---|---|---|
| WO | WO-2014/205389 A1 | 12/2014 |
| WO | WO-2014/205393 A1 | 12/2014 |
| WO | WO-2016/025904 A1 | 2/2016 |
| WO | WO-2017/117529 A1 | 7/2017 |
| WO | WO-2017/117535 A1 | 7/2017 |
| WO | WO-2018/098472 A1 | 5/2018 |
| WO | WO-2018/129227 A1 | 7/2018 |

OTHER PUBLICATIONS

Balsamini, "(E)-3-(2-(N-Phenylcarbamoyl)vinyl)pyrrole-2-carboxylic Acid Derivatives. A Novel Class of Glycine Site Antagonists", Journal of Medicinal Chemistry, 41(6):808-820 (Jan. 1, 1998).
Brekhov, Y. et al., "Cyanomethyltetrazoles II reactions of the methylene Fragment", Zhurnal organicheskoi Khimii, 28(9): 1921-1925 (1992).
Brittain, "Drugs in Pharmaceutical Sciences, v. 192. Polymorphism in Pharmaceutical Solids," CRC Press (2009).
Bryn, "Pharmaceutical Solids: A Strategic Approach to Regulatory Considerations," Pharma Res 12(7):945-954 (1995).
Buckler, R.T. et al., "Synthesis and Antiinflammatory Activity of Some 1,2,3- and 1,2,4-Triazolepropionic Acids", Journal of Medicinal Chemistry, 21(12): 1254-1260 (1978).
Burdeska et al., "Anil-Synthese. 23. Mitteilung. Ueber die Herstellung von Styryl- und Stilbenyl-Derivaten des Pyrimidins // Anil synthesis. Part 23. Preparation of styryl and stilbenyl derivatives of pyrimidines," Helv Chim Acta, 64(1): 113-152 (1981).
Cai, X., et al., "Inhibition of Thr-55 phosphorylation restores p53 nuclear localization and sensitizes cancer cells to DNA damage", Proc Nat Acad Sci, 105(44):16958-16963 (2008).
Cancer [online], [retrieved on Jul. 6, 2007] Retrieved from the Internet, URL: http://www.nlm.nih.gov/medlineplus/cancer.html (Year: 2007).
Cantu et al., "Using the Selective Inhibitor of Nuclear Export (SINE) Compound KPT-350 to Reduce Cortical Circuit Hyperexcitability and Interneuron Cell Loss in the Controlled Cortical Impact (CCI) Model of Traumatic Brain Injury (TBI) (I11.001)," Neurology, 86(16 Supplement):IT1.001 (2016).
ChemCats RN# 1035122-02-1; Publicly available on Jul. 12, 2009.
ChemCats RN# 1134927-58-4; Publicly available on Apr. 15, 2009.
ChemCats RN# 930886-49-0; Publicly available on Apr. 29, 2007.
Cheng et al., "XPO1 (CRM1) Inhibition Represses STAT3 Activation to Drive a Survivin-Dependent Oncogenic Switch in Triple-Negative Breast Cancer," Mol Cancer Ther 13(3):675-686 (2014).
Cooper et al., "Synthesis of Some 1,2,4-Triazoles and 1,2,4-Triazolines by Reaction of Oxamidrazone Condensation Products with Acetic Anhydride," Journal of Chemical Society Perkin Transactions 1, 15: 1433-1437 (1975).
Cronshaw, J.M. et al., "The nuclear pore complex: disease associations and functional correlations", Trends Endocrin Metab. 15:34-39 (2004).
Daelemans, D. et al., "A synthetic HIV-1 Rev inhibitor interfering with the CRM1-mediated nuclear export", PNAS, 99(22):14440-14445 (2002).
Database PubChem Compound, Database Accession No. 33777540 (May 29, 2009), 3 pages.
Database PubChem Compound, Database Accession No. 33777561 (May 29, 2009), 3 pages.
Database PubChem Compound, Database Accession No. 33777585 (May 29, 2009), 3 pages.
Database PubChem Compound, Database Accession No. 66525271 (Oct. 24, 2012), 3 pages.
Database PubChem Compound, Database Accession No. 66525276 (Oct. 24, 2012), 3 pages.
Database PubChem Compound, Database Accession No. 72062355 (2007), 11 pages.
Database PubChem Compound, Database Accession No. 940775133 (Jul. 7, 2017), 1 page.
Davis, J.R. et al., "Controlling protein compartmentalization to overcome disease" Pharmaceut Res., 24:17-27 (2007).
Dorwald, "Side Reactions in Organic Synthesis: A Guide to Successful Synthesis Design," Wiley-VCH Verlag GmbH & Co. KGaA, Weinheim (2005).
Etchin et al., "KPT-330 inhibitor of CRM1 (XPO1)-mediated nuclear export has selective anti-leukaemic activity in preclinical models of T-cell acute lymphoblastic leukaemia and acute myeloid leukaemia," British Journal of Haematology, 161:117-127 (2013).
Extended European Search Report for EP Application No. 17189480.1 dated May 16, 2018.
Extended European Search Report for EP Application No. EP 18202641 dated Feb. 15, 2019.
Extended European Search Report issued by the European Patent Office in corresponding European Application No. 18164757.0 dated Aug. 8, 2018.
Extended Search Report for EP Application No. 11751491.9, "Nuclear Transport Modulators and Uses Thereof", Date of Completion of the Search: Dec. 17, 2013. 6 pages.
Extended Search Report for EP Application No. 12736172.3, "Olefin Containing Nuclear Transport Modulators And Uses Thereof", Date of Completion of the Search: May 8, 2014. 3 pages.
Falini, B. et al., "Both carboxy-terminus NES motif and mutated tryptophan(s) are crucial for aberrant nuclear export of nucleophosmin leukemic mutants in NPMc+ AML", Blood Journal, 107(11):4514-4523 (2013).
Freundt, E.C. et al., "Molecular Determinants for Subcellular Localization of the Severe Acute Respiratory Syndrome Coronavirus Open Reading Frame 3b Protein", Journal of Virology, 83(13):6631-6640 (Jul. 2009).
Ghildyal, R. et al., "The Respiratory Syncytial Virus Matrix Protein Possesses a Crm1-Mediated Nuclear Export Mechanism", Journal of Virology, 83(11):5353-5362 (2009).
Ghosh, C.C. et al., "Analysis of nucleocytoplasmic shuttling of NF kappa B proteins in human leukocytes", Methods Mol. Biol. 457:279-92 (2008).
Golub, T.R. et al., "Molecular Classification of Cancer: Class Discovery and Class Prediction by Gene Expression Monitoring", Science, 286: 531-537 (1999).
Gravina et al., "XPO1/CRM1-Selective inhibitors of nuclear export (SINE) reduce tumor spreading and improve overall survival in preclinical models of prostate cancer (PCa)," Journal of Hematology & Oncology, 7(46):1-17 (2014).
Gupta, N. et. al., "Retinal tau pathology in human glaucomas" Can J Ophthalmol. 43(1):53-60 (2008).
Haines et al., "Selective Inhibitors of Nuclear Export Avert Progression in Preclinical Models of Inflammatory Demyelination," Nature Neuroscience, 18(4): 511-520 (2015).
Hilliard et al., "The anti-inflammatory prostaglandin 15-Deoxy-Δ12,14 PGJ2 inhibits CRM1-dependent nuclear protein export," Journal of Biological Chemistry, 1-12 (2010).
Hoffman et al., "Synthesis of Vinyl-Functionalized Oxazoles by Olefin Cross-Metathesis", J. Org. Chem. 73: 2400-2403 (2008).
Hoshino, I. et al., "Combined effects of p53 gene therapy and leptomycin B in human esophageal squamous cell carcinoma", Oncology, 75:113-119 (2008).
Huff, J., "HIV Protease: A Novel Chemotherapeutic Target for AIDS", Journal of Medicinal Chemistry, 34(8): 2305-2314 (1991).
International Preliminary Report on Patentability for International Application No. PCT/US2011/027328, "Nuclear Transport Modulators and Uses Thereof" dated Sep. 11, 2012.
International Preliminary Report on Patentability for International Application No. PCT/US2012/021406, "Olefin Containing Nuclear Transport Modulators and Uses Thereof" dated Jul. 17, 2013.
International Preliminary Report on Patentability for International Application No. PCT/US2014/029322 dated Sep. 15, 2015.
International Preliminary Report on Patentability for International Application No. PCT/US2014/043479, dated Dec. 22, 2015.
International Preliminary Report on Patentability for International Application No. PCT/US2014/043484, dated Dec. 22, 2015.

(56) References Cited

OTHER PUBLICATIONS

International Preliminary Report on Patentability for International Application No. PCT/US2015/045395 dated Feb. 21, 2017.
International Preliminary Report on Patentability for International Application No. PCT/US2016/069492 dated Jul. 3, 2018.
International Preliminary Report on Patentability for International Application No. PCT/US2016/069508 dated Jul. 3, 2018.
International Preliminary Report on Patentability for International Application No. PCT/US2017/063439 dated May 28, 2019.
International Preliminary Report on Patentability for International Application No. PCT/US2012/048319, "Hydrazide Containing Nuclear Transport Modulators and Uses Thereof"; Date of Issuance of the Report: Feb. 4, 2014.
International Preliminary Report on Patentability for International Application No. PCT/US2012/048368, "Nuclear Transport Modulators and Uses Thereof"; Date of Issuance of the Report: Feb. 4, 2014.
International Preliminary Report on Patentability for International Application No. PCT/US2013/040404, "Nuclear Transport Modulators and Uses Thereof"; Date of Issuance of the Report: Nov. 11, 2014.
International Search Report and The Written Opinion of the International Searching Authority for International Application No. PCT/US2012/021406, "Olefin-Containing Nuclear Transport Modulators and Uses Thereof" dated Apr. 30, 2012.
International Search Report and The Written Opinion of the International Searching Authority for International Application No. PCT/US2012/049470, "Maleimide Compounds and Methods of Treatment," dated Feb. 13, 2013.
International Search Report and The Written Opinion of the International Searching Authority for International Application No. PCT/US2013/040404, "Nuclear Transport Modulators and Uses Thereof"; dated Nov. 18, 2013.
International Search Report and the Written Opinion of the International Searching Authority, or the Declaration for International Application No. PCT/US2014/027136 "Exo Olefin-Containing Nuclear Transport Modulators and Uses Thereof"; dated Jul. 11, 2014.
International Search Report and the Written Opinion of the International Searching Authority, or the Declaration for International Application No. PCT/US2014/029322 "Methods of Promoting Wound Healing Using CRM1 Inhibitors"; dated May 28, 2014.
International Search Report and the Written Opinion of the International Searching Authority, or the Declaration for International Application No. PCT/US2014/043479 "Nuclear Transport Modulators and Uses Thereof"; dated Sep. 17, 2014.
International Search Report and the Written Opinion of the International Searching Authority, or the Declaration for International Application No. PCT/US2014/043484 "Nuclear Transport Modulators and Uses Thereof"; dated Sep. 2, 2014.
International Search Report and Written Opinion for International Application No. PCT/US2015/045395 dated Jan. 12, 2016.
International Search Report and Written Opinion for International Application No. PCT/US2016/069492 dated Feb. 16, 2017.
International Search Report and Written Opinion for International Application No. PCT/US2016/069508 dated May 23, 2017.
International Search Report and Written Opinion for International Application No. PCT/US2017/063439 dated Feb. 2, 2018.
International Search Report for International Application No. PCT/US2011/027328, "Nuclear Transport Modulators and Uses Thereof" dated Apr. 29, 2011.
International Search Report for International Application No. PCT/US2012/048319, "Hydrazide Containing Nuclear Transport Modulators and Uses Thereof" dated Nov. 9, 2012.
International Search Report for International Application No. PCT/US2012/048368, "Nuclear Transport Modulators and Uses Thereof" dated Sep. 21, 2012.
Jiang et al., "Palladium-Catalyzed Alkenylation of 1,2,3-Trizoles with Terminal Conjugated Alkenes by Direct C—H Bond Functionalization," Eur J Org Chem, 7:1227-30 (2010).

Karyagin, A. Yu., Reagents for addressed modification of biopolymers, Russian Chemical Bulletin, 2000, 49(3):540-5.
Karyopharm Therapeutics, "Karyopharm Presents Data Demonstrating the Potential of Nuclear Export Protein Exportin 1 (XPO1) Inhibition in the Treatment of Traumatic Brain Injury," Apr. 20, 2016, Retrieved from the Internet: http://investors.karyopharm.com/static-files/577eb861-4183-463a-9a5b-d0f1def1629d [retrieved on Jan. 25, 2018].
Kau, T.R. et al., "A chemical genetic screen identifies inhibitors of regulated nuclear export of a Forkhead transcription factor in PTEN-deficient tumor cells", Cancer Cell, pp. 463-476 (2003).
Kaur et al., "Tyrphostin Induced Growth Inhibition: Correlation with Effect on p210bcr-abl Autokinase Activity in K562 Chronic Myelogenous Leukemia," Anti-Cancer Drugs, 5(2): 213-222 (1994).
Lain, S. et al., "Accumulating active p53 in the nucleus by inhibition of nuclear export: a novel strategy to promote the p53 tumor suppressor function", Exp Cell Res. 253: 315-324 (1999).
Lain, S. et al., "An inhibitor of nuclear export activates the p53 response and induces the localization of HDM2 and p53 to U1A-positive nuclear bodies associated with the PODs", Exp Cell Res. 248:457-472 (1999).
Lala, P.K. et al., "Role of nitric oxide in tumor progression: Lessons from experimental tumors", Cancer and Metastasis Reviews, 17: 91-106 (1998).
Lapalombella, R. et al., "Selective Inhibitors of nuclear exports show that CRM1/XPO1 is a target in chronic lymphocytic leukemia", Blood, 120(23): 4621-4634 (Nov. 29, 2012).
Li, A. et al., "Upregulation of CRM1 Relates to Neuronal Apoptosis after Traumatic Brain Injury in Adult Rats", J Mol Neurosci, 51(1):208-218 (2013).
Maekawa et al., "Efficient Formation of a Triazole Ring Via Novel Ring-Opening Reaction of (z)-2-Methyl-4-arylmethylene-5(4H)-Oxazolones with Hydrazides," Heterocycles, 75(12): 2959-2971 (2008).
Maga et al., "Pharmacophore modeling and molecular docking led to the discovery of inhibitors of human immunodeficiency virus-1 replication targeting the human cellular aspartic acid-glutamic acid-alanine-aspartic acid box polypeptide 3," J Med Chem, 51(21):6635-8 (2008).
Marelli et al., "Tumor targeting via integrin ligands," Frontiers in Oncology, 3(222):1-12 (2013).
Miskolci et al., "TNFα release from peripheral blood leukocytes depends on a CRM1-mediated nuclear export," Biochemical and Biophysical Research Communications, 351:354-360 (2006).
Modzelewska-Banachiewicz, B. et al., "Synthesis and biological activity of (Z) and (E) isomers of 3-(3,4-diaryl-1,2,4-triazole-5-yl)prop-2-enoic acid" Monatsh Chem. 140:439-444 (2009).
Modzelewska-Banachiewicz, B. et al., "Synthesis and biological activity of new derivatives of 3-(3,4-diaryl-1,2,4-triazole-5-yl)propenoic acid" European Journal of Medicinal Chemistry, 39:873-877 (2004).
Monecke, T. et al., "Crystal Structure of the Nuclear Export Receptor CRM1 in Complex with Snurportin1 and RanGTP", Science, 324:1087-1091 (2009).
Morales et al., "Mechanical Particle-Size Reduction Techniques, Formulating Poorly Water Soluble Dugs," AAPS Advances in Pharmaceutical Sciences Series, 133-170 (2012).
Morissette et al., "High-throughput crystallization: polymorphs, salts, co-crystals and solvate of pharmaceutical solids," Adv Drug Deliv Rev, 56(3):275-300 (2004).
Muller, P.A.J. et al., "Nuclear-Cytosolic Transport of COMMD1 Regulates NF-κB and HIF-1 Activity", Traffic, 10:514-527 (2009).
Mutka et al., "Identification of Nuclear Export Inhibitors with Potent Anticancer Activity in Vivo," Cancer Research, 69(2): 510-517 (2009).
Mutka, S. et al., "Nuclear export inhibitors (NEIs) as novel cancer therapeutics", 98th AACr Ann. Mtg., 2 pgs (Apr. 14-18, 2007) (Poster).
Nagase, The Practice of Medicinal Chemistry, Chapter 13. Conversion of Molecules Based on Equivalent Substitution, vol. 1, Technomics Inc., 1998, 253.
Nair, V., "Thermally induced skeletal rearrangement in a triazepine," J Heterocyclic Chem, 12(1):183-4 (1975).

(56) References Cited

OTHER PUBLICATIONS

Nakahara, J. et al., "Abnormal expression of TIP30 and arrested nucleocytoplasmic transport within oligodendrocyte precursor cells in multiple sclerosis", Journal of Clinical Investigation, 119(1):169-181 (2009).
Nautiyal et al., "Distinct functions for RIP140 in development, inflammation, and metabolism," Trends in Endocrinology and Metabolism, 24(9):451-459 (2013).
Noske, A., et al., "Expression of the Nuclear Export Protein Chromosomal Region Maintenance/Exportin 1/Xpo1 Is a Prognostic Factor in Human Ovarian Cancer", Cancer, 112(8):1733-1743 (2008).
Orsted et al., "Basic principles of wound healing," Wound Care Canada, 9(2): 4-12 (2011).
Patani, G.A., et al., "Bioisosterism: A Rational Approach in Drug Design", Chem Rev, 96:3147-3176 (1996).
Procopiou et al., "Inhibitors of Cholesterol Biosynthesis. 2. 3,5-Dihydroxy-7-(N-pyrrolyl)-6-heptenoates, a Novel Series of HMG-CoA Reductase Inhibitors," J Med Chem, 36(23): 3658-3662 (1993).
Quan, M.L. et al., "Design and Synthesis of Isoxazoline Derivatives as Factor Xa Inhibitors", J. Med. Chem. 42: 2760-2773 (1999).
Rawlinson, S.M. et al., "CRM1-mediated Nuclear Export of Dengue Virus RNA Polymerase NS5 Modulates Interleukin-8 Induction and Virus Production", Journal of Biological Chemistry, 284(23):15589-15597 (2009).
Registry(STN)[online], Jan. 23, 2008, CAS registered No. 1000508-38-2, 1 page.
Sakamoto et al., "Studies on Pyrimidine Derivatives. XXV. Reaction of Pyrimidinyl Aldehydes and Ketones with Wittig Reagents," Chem Pharm Bull, 30(2): 610-614 (1982).
Sanchez, V. et al., "Nuclear Export of the Human Cytomegalovirus Tegument Protein pp65 Requires Cyclin-Dependent Kinase Activity and the Crm1 Exporter", Journal of Virology, 81(21):11730-11736 (2007).
Shaoyong, Ke. et al., "Research Advance of Acylhydrazine Derivatives with Biological Activities", Chinese Journal of Organic Chemistry 30(12):1820-1830 (2010).
Shasheva, "Reactions of Hydroxyphenyl-Substituted 1,2,4-Triazoles with Electrophilic Reagents", Russian Journal of General Chemistry, 79(10): 2234-2243 (2009).
Sorokin, A.V. et al., "Nucleocytoplasmic Transport of Proteins", Biochemistry Moscow, 72(13):1439-1457 (2007).
Storey et al., "Solid State Characterization of Pharmaceuticals," Blackwell Publishing, (2011).
Sun Q., et al., "Nuclear export inhibition through covalent conjugation and hydrolysis of Leptomycin B by CRM1", Proc Nat Acad Sci, 110(4): 1303-1308 (2013).
Tai et al., "CRM1 inhibition induces tumor cell cytotoxicity and impairs osteoclastogenesis in multiple myeloma: molecular mechanisms and therapeutic implications," Leukemia, 28:155-165 (2014).
Tamir et al., "KPT-350, a Selective Inhibitor of Nuclear Export (SINE) Compound, Shows Efficacy in the Mouse Pilocapine Model of Temporal Lobe Epilepsy," Journal of Neurological Sciences, 381:87-88 (2017).
Terry, L.J. et al., "Crossing the Nuclear Envelope: Hierarchical Regulation of Nucleocytoplasmic Transport", Science, 318:1412-1416 (2007).
Van der Watt, P.J. et al., "The Karyopherin proteins, Crm1 and Karyopherin β1, are overexpressed in cervical cancer and are critical for cancer cell survival and proliferation", Int. J. Cancer, 124:1829-1840 (2009).
Van Neck et al., "Inhibition of the CRM1-mediated nucleocytoplasmic transport by N-azolylacrylates: Structure-activity relationship and mechanism of action", Bioorganic & Medicinal Chemistry 16:9487-9497 (2008).
Walsh, Jr., M.D., et al., Exportin 1 Inhibition Attenuates Nuclear Factor-κB-Dependent Gene Expression, Shock, 29(2):160-166 (2008).
Wang et al., "Mathematical modeling in cancer drug discovery," Drug Discovery Today, 19(2):145-150 (2014).
Williams, P., et al., "Characterization of a CRM1-Dependent Nuclear Export Signal in the C Terminus of Herpes Simplex Virus Type 1 Tegument Protein UL47", Journal of Virology, 82(21):10946-10952 (2008).
Written Opinion of the International Searching Authority for International Application No. PCT/US2011/027328, "Nuclear Transport Modulators and Uses Thereof" dated Apr. 29, 2011, 8 pages.
Written Opinion of the International Searching Authority for International Application No. PCT/US2012/048319, "Hydrazide Containing Nuclear Transport Modulators and Uses Thereof" dated Nov. 9, 2012, 9 pages.
Written Opinion of the International Searching Authority for International Application No. PCT/US2012/048368, "Nuclear Transport Modulators and Uses Thereof" dated Sep. 21, 2012, 11 pages.
Yao, Y., et al., "The expression of CRM1 is associated with prognosis in human osteosarcoma", Oncology Reports, 21:229-235 (2009).
Zheng et al., "KPT-330 inhibitor of XPO1-mediated nuclear export has anti-proliferative activity in hepatocellular carcinoma," Cancer Chemother Pharmacol, 74:487-495 (2014).
Zimmerman, T.L. et al., "Nuclear Export of Retinoid X Receptor α in Response to Interleukin-1β-mediated Cell Signaling Roles for JNK and Ser260", The Journal of Biological Chemistry, 281(22):15434-15440 (2006).

* cited by examiner

CRM1 INHIBITORS FOR TREATING EPILEPSY

RELATED APPLICATION

This application is the U.S. National Stage of International Application No. PCT/US2017/063439, filed Nov. 28, 2017, which designates the U.S., published in English, and claims the benefit of U.S. Provisional Application No. 62/426,957, filed on Nov. 28, 2016. The entire teachings of the above applications are incorporated herein by reference.

BACKGROUND OF THE INVENTION

Epilepsy is a chronic brain disease in which unprovoked epileptic seizures are the predominant feature. Epileptic seizures are episodes that can vary from brief and nearly undetectable to long periods of vigorous shaking. In epilepsy, seizures tend to recur, and have no immediate underlying cause. Epileptic seizures are the result of increased and irregular nerve cell activity in the cortex of the brain. Diagnosis may involve imaging the brain and performing blood tests. Epilepsy can often be confirmed with an electroencephalogram (EEG), but a normal test does not rule out the condition.

Epilepsy and its related syndromes may be classified according to whether the associated seizures are partial or generalized, and whether the etiology is idiopathic or symptomatic or cryptogenic. Several important syndromes can be further grouped according to age of onset and prognosis. The most common type (60%) of seizures is convulsive. Of these, one-third begins as generalized seizures from the start, affecting both hemispheres of the brain. Two-thirds begin as partial seizures (which affect one hemisphere of the brain) which may then progress to generalized seizures. The remaining 40% of seizures are non-convulsive.

In epileptic seizures, a group of excitory neurons begin firing in an abnormal, excessive, and synchronized manner. This results in a wave of depolarization known as a paroxysmal depolarizing shift. Normally, after an excitatory neuron fires, it becomes more resistant to firing for a period of time. This is due in part to the effect of inhibitory neurons, electrical changes within the excitatory neuron, and the negative effects of adenosine. However, in epilepsy, the excitatory neurons are less resistant to further firing which can result in seizure activity.

Generally, most epilepsies and diseases/disorders associated therewith are difficult to treat, since epilepsies are not etiologically elucidated. Thus, administration of an antiepileptic agent is a common approach toward suppressing epileptic seizures or inhibiting propagation of focal seizures to other areas.

Seizures are controllable with medication in about 70% of cases. The older established antiepileptic drugs (AEDs) such as phenytoin carbamazepine, clonazepam, ethosuximide, valproic acid and barbiturates are widely prescribed but suffer from a range of side effects. Furthermore, there is a significant group of patients (20-30%) that are resistant to the currently available therapeutic agents. Fifty million people in the world have epilepsy, and there are between 16 and 51 cases of new-onset epilepsy per 100,000 people every year. Patients with drug-resistant epilepsy have an increased risk of premature death, injuries, psychosocial dysfunction, and a reduced quality of life.

People with epilepsy are at an increased risk of death. This increase is between 1.6 and 4.1 fold greater than that of the general population and is often related to the underlying cause of the seizures, status epilepticus, suicide, trauma, and sudden unexpected death in epilepsy (SUDEP). The risk of suicide is increased between two and six times in those with epilepsy compared to the general population.

In view of the foregoing, a great need exists for the discovery of methods for treating epilepsy in a subject that has, for example, either or both of partial and generalized seizures.

SUMMARY OF THE INVENTION

The invention generally relates to the use of nuclear transport modulators, e.g., CRM1 inhibitors, of Formula (I) for treating epilepsy in a subject. Subjects can have unprovoked seizures without prior warning that affect one or both hemispheres of the brain. The disclosed methods can reduce the severity and occurrence of these unprovoked epileptic seizures and can result in resolution of epilepsy.

One embodiment provides a method for treating epilepsy in a subject in need thereof, the method comprising administering to the subject an effective amount of a compound represented by Formula (I):

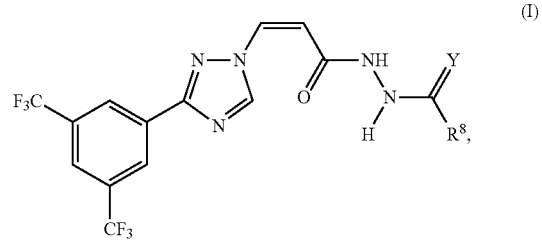

or a pharmaceutically acceptable salt thereof, wherein:
Y is O;
$R^8$ is selected from —N($R^9$)—($C_3$-$C_6$ cycloalkyl), —$C_3$-$C_6$ alkyl, —($C_0$-$C_1$ alkylene)-heterocyclyl, and —($C_0$-$C_1$ alkylene)-heteroaryl;
$R^9$ is selected from hydrogen and $C_1$-$C_4$ alkyl;
wherein: any alkyl or alkylene portion of any $R^8$ is optionally and independently substituted, for example with one or more substituents selected from oxo and —N($R^7$)$_2$, wherein each $R^7$ is independently selected from hydrogen and $C_1$-$C_4$ alkyl;
any heterocyclyl portion of $R^8$ comprises at least one nitrogen atom in a ring, and is optionally substituted with one or more substituents for example subsituents selected from $C_1$-$C_4$ alkyl and oxo; and
any heteroaryl portion of $R^8$ comprises at least one nitrogen atom in a ring and is optionally substituted with one or more substituents, for example, a $C_1$-$C_4$ alkyl.

In a particular embodiment, the epilepsy can be characterized as having unprovoked partial or generalized seizures. These seizures can be convulsive or non-convulsive. There are six main categories of seizures that are categorized by their type and duration: tonic-clonic, tonic, clonic, myoclonic, absence, and atonic seizures.

Also provided herein are compounds represented by structural Formula (I), and compounds of Table 1 for use in treating epilepsy and for use in the manufacture of a medicament for treating epilepsy.

The novel features of the present invention will become apparent to those of skill in the art upon examination of the following detailed description of the invention. It should be understood, however, that the detailed description of the invention and the specific examples presented, while indicating certain embodiments of the present invention, are provided for illustration purposes only because various changes and modifications within the spirit and scope of the invention will become apparent to those of skill in the art from the detailed description of the invention and claims that follow.

DETAILED DESCRIPTION OF THE INVENTION

Figure 1:
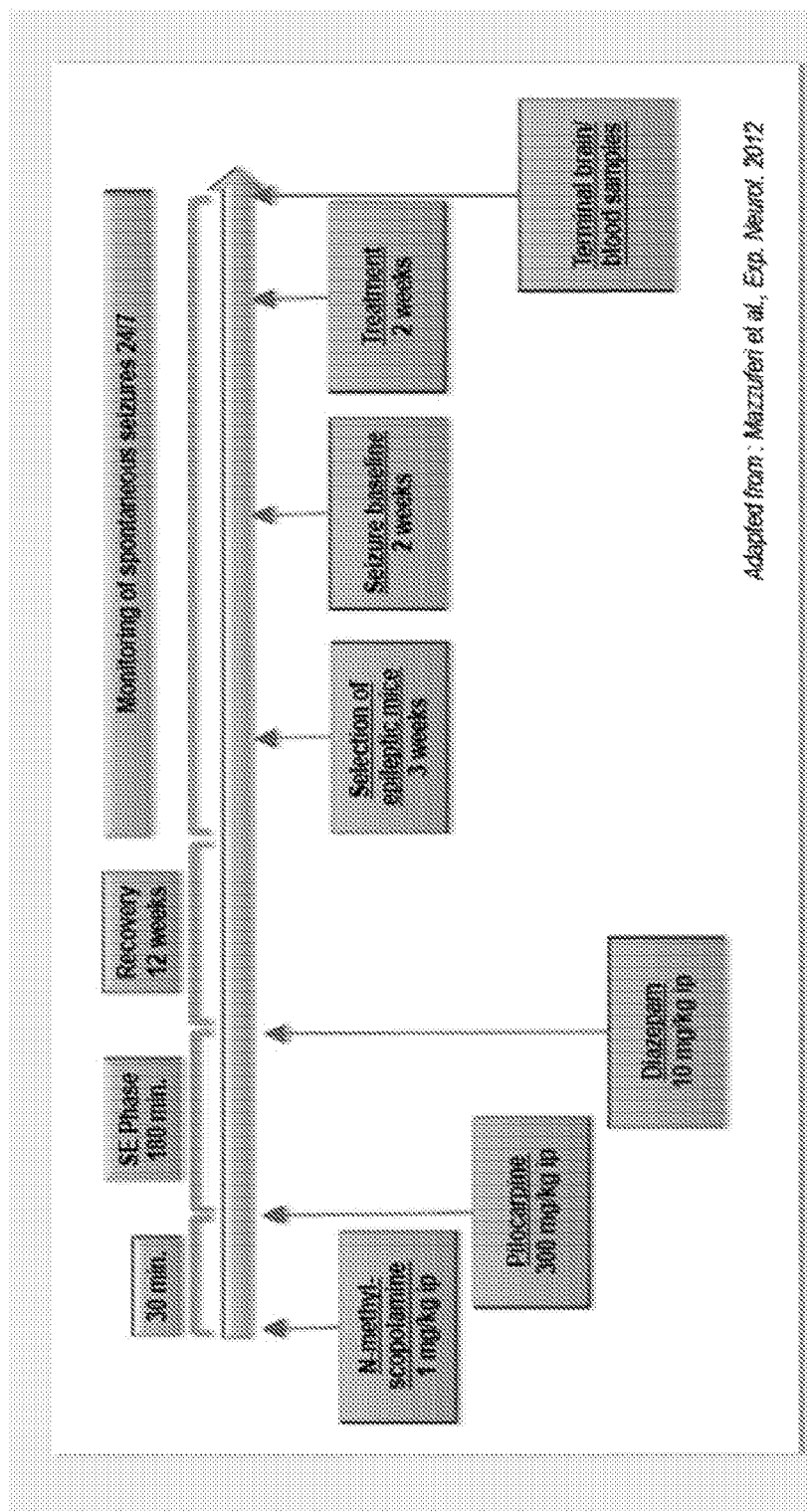
FIG. 1 is a description of a pilocarpine model of temporal lobe epilepsy (TLE) in male NMRI mice. The treatment phase was compound E-1 in Table I administered at 7.5 mg/kg per os or vehicle, every other day for the two week treatment period. Vehicle was 0.6% plasdone PVP K29/32 and 0.6% poloxamer Pluronic F68 in water.
Figure 2:
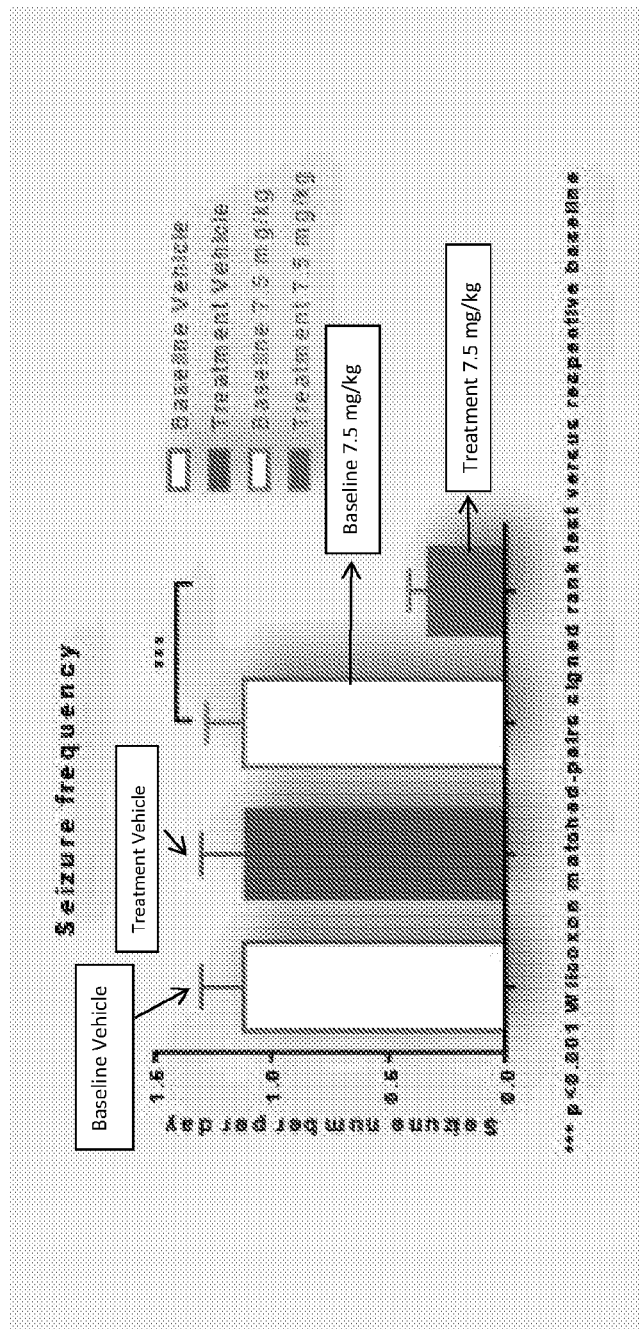
FIG. 2 shows the effects of chronic administration of compound E-1 on seizure recurrence in mice subjected to the pilocarpine model of TLE.
Figure 3:
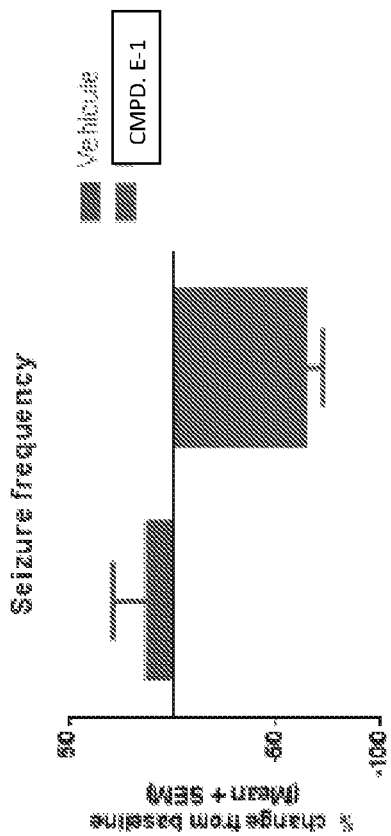
FIG. 3 shows the effects of chronic administration of compound E-1 on seizure recurrence in mice subjected to the pilocarpine model of TLE.
Figure 4:
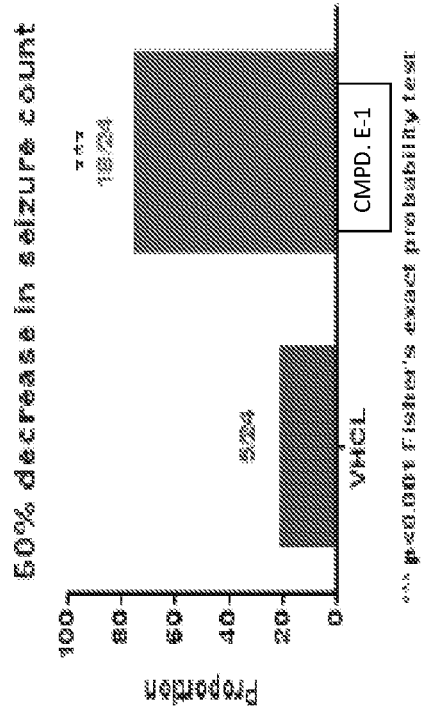
FIG. 4 shows the effects of chronic administration of compound E-1 on seizure recurrence. A significant number of mice showed a 50% reduction in seizure occurrence in comparison to vehicle treated mice.
Figure 5:
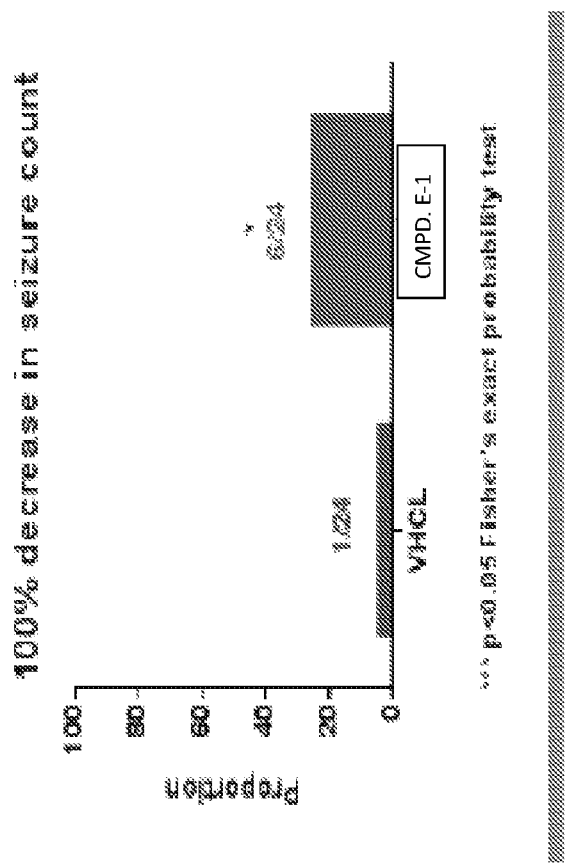
FIG. 5 shows the effects of chronic administration of compound E-1 on seizure recurrence. Six mice showed a 100% reduction in seizure activity.

A description of exemplary embodiments of the invention follows.

Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

Unless specified otherwise within this specification, the nomenclature used in this specification generally follows the examples and rules stated in Nomenclature of Organic Chemistry, Sections A, B, C, D, E, F, and H, Pergamon Press, Oxford, 1979, which is incorporated by reference herein for its exemplary chemical structure names and rules on naming chemical structures. Optionally, a name of a compound may be generated using a chemical naming program such as ACD/ChemSketch, Version 5.09/September 2001, Advanced Chemistry Development, Inc., Toronto, Canada, or Chem Draw, Versions 15.1 and lower, PerkinElmer, Waltham, Mass.

If there is a discrepancy between a structural formula of a compound and the name of a compound, the structural formula should be assumed correct.

Compounds of the present invention may have asymmetric centers, chiral axes, and chiral planes (e.g., as described in: E. L. Eliel and S. H. Wilen, Stereo-chemistry of Carbon Compounds, John Wiley & Sons, New York, 1994, pages 1119-1190), and occur as racemates, racemic mixtures, and as individual diastereomers or enantiomers, with all possible isomers and mixtures thereof, including optical isomers, being included in the present invention.

The term "aliphatic" or "aliphatic group," as used herein, denotes a monovalent hydrocarbon radical that is straight-chain (i.e., unbranched), branched, or cyclic (including fused, bridged, and spiro-fused polycyclic). An aliphatic group can be saturated or can contain one or more units of unsaturation, but is not aromatic. Unless otherwise specified, aliphatic groups contain 1-6 carbon atoms. However, in some embodiments, an aliphatic group contains 1-10 or 2-8 carbon atoms. In some embodiments, aliphatic groups contain 1-4 carbon atoms and, in yet other embodiments, aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl. An aliphatic group can be optionally substituted as described herein.

The term "alkyl," as used herein, means a saturated, straight-chain or branched aliphatic group. In one aspect, an alkyl group contains 1-6 or 1-4 carbon atoms. Alkyl includes, but is not limited to, methyl, ethyl, propyl, isopropyl, n-butyl, sec-butyl, t-butyl, and the like. An alkyl group can be optionally substituted as described herein.

The term "alkenyl," as used herein, means a straight-chain or branched aliphatic group having one or more carbon-carbon double bonds (i.e., —CH=CH—). In one aspect, an alkenyl group has from two to four carbon atoms, and includes, for example, and without being limited thereto, ethenyl, 1-propenyl, 1-butenyl and the like. The term "alkenyl" encompasses radicals having carbon-carbon double bonds in the "cis" and "trans" or, alternatively, the "E" and "Z" configurations. If an alkenyl group includes more than one carbon-carbon double bond, each carbon-carbon double bond is independently a cis or trans double bond, or a mixture thereof. An alkenyl group can be optionally substituted as described herein.

The term "alkynyl," as used herein, means a straight-chain or branched aliphatic radical having one or more carbon-carbon triple bonds (i.e., —C≡C—). In one aspect, an alkyl group has from two to four carbon atoms, and includes, for example, and without being limited thereto, 1-propynyl (propargyl), 1-butynyl and the like. An alkynyl group can be optionally substituted as described herein.

The terms "cycloaliphatic," "carbocyclyl," "carbocyclo," and "carbocyclic," used alone or as part of a larger moiety, refer to a saturated or partially unsaturated cyclic aliphatic monocyclic or bicyclic ring system, as described herein, having from 3 to 12 members, wherein the aliphatic ring system is optionally substituted as defined above and described herein. In some embodiments, a cycloaliphatic group has 3-6 carbon atoms. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. The terms "cycloaliphatic," "carbocyclyl," "carbocyclo," and "carbocyclic" also include aliphatic rings that are fused to one or more aromatic or nonaromatic rings, such as decahydronaphthyl, tetrahydronaphthyl, decalin, or bicyclo[2.2.2]octane. These aliphatic rings can be optionally substituted as described herein.

The term "cycloalkyl," as used herein, means a saturated cyclic aliphatic monocyclic or bicyclic ring system having from 3-12 members. A cycloalkyl can be optionally substituted as described herein. In some embodiments, a cycloalkyl has 3-6 carbons. A cycloalkyl group can be optionally substituted as described herein.

The term "heterocyclyl," as used herein, means a saturated or unsaturated aliphatic ring system having from 3 to 12 members in which at least one carbon atom is replaced with a heteroatom selected from N, S and O. A heterocyclyl can contain one or more rings, which may be attached together in a pendent manner or may be fused. In one aspect, a heterocyclyl is a three- to seven-membered ring system and includes, for example, and without being limited thereto, piperidinyl, piperazinyl, pyrrolidinyl, tetrahydrofuranyl and the like. A heterocyclyl group can be optionally substituted as described herein.

The term "heteroatom" means one or more of oxygen, sulfur, nitrogen, phosphorus, or silicon, and includes any oxidized form of nitrogen, sulfur, phosphorus, or silicon; the quaternized form of any basic nitrogen; and a substitutable nitrogen of a heterocyclic ring, for example N (as in 3,4-dihydro-2H-pyrrolyl), NH (as in pyrrolidinyl) or NR$^+$ (as in N-substituted pyrrolidinyl).

The term "unsaturated," as used herein, means that a moiety has one or more units of unsaturation.

The term "alkoxy," as used herein, means —O-alkyl. "Alkoxy" can include a straight-chained or branched alkyl. In one aspect, "alkoxy" has from one to eight carbon atoms and includes, for example, and without being limited thereto, methoxy, ethoxy, propyloxy, isopropyloxy, t-butoxy and the like. An alkoxy group can be optionally substituted as described herein.

The term "halo" or "halogen" as used herein means halogen and includes, for example, and without being limited thereto, fluoro, chloro, bromo, iodo and the like, in both radioactive and non-radioactive forms.

The term "haloalkyl," as used herein, means an alkyl group that is substituted with one or more halogen atoms. In some embodiments, haloalkyl refers to a perhalogenated alkyl group. In some embodiments, haloalkyl refers to an alkyl group which is substituted with one or more halogen atoms. Exemplary haloalkyl groups include —CF$_3$, —CF$_2$H, —CCl$_3$, —CF$_2$CH$_3$, —CH$_2$CF$_3$, —CH$_2$(CF$_3$)$_2$, —CF$_2$(CF$_3$)$_2$, and the like. Preferred haloalkyl groups include —CF$_3$ and —CF$_2$H. A preferred haloalkyl group is —CF$_3$.

The term "alkylene," as used herein, means a bivalent branched or unbranched saturated hydrocarbon radical. In one aspect, "alkylene" has one to six carbon atoms, and includes, for example, and without being limited thereto, methylene, ethylene, n-propylene, n-butylene and the like. An alkylene group can be optionally substituted as described herein.

The term "alkenylene," as used herein, means a bivalent branched or unbranched hydrocarbon radical having one or more carbon-carbon double bonds (i.e., —CH=CH—). In one aspect, "alkenylene" has two to six carbon atoms, and includes, for example, and without being limited thereto, ethenylene, n-propenylene, n-butenylene and the like. An alkenylene group can be optionally substituted as described herein.

The term "alkynylene," as used herein, means a bivalent branched or unbranched hydrocarbon radical having one or more carbon-carbon triple bonds (i.e., —C≡C—). In one aspect, "alkynylene" has two to six carbon atoms, and includes, for example, and without being limited thereto, ethynylene, n-propynylene, n-butynylene and the like. An alkynylene group can be optionally substituted as described herein.

The term "aryl," alone or in combination, as used herein, means a carbocyclic aromatic system containing one or more rings, which may be attached together in a pendent manner or may be fused. In some embodiments, an aryl has one, two or three rings. In one aspect, the aryl has six to twelve ring atoms. The term "aryl" encompasses aromatic radicals such as phenyl, naphthyl, tetrahydronaphthyl, indanyl, biphenyl, phenanthryl, anthryl and acenaphthyl. An "aryl" group can have 1 to 4 substituents, such as lower alkyl, hydroxyl, halo, haloalkyl, nitro, cyano, alkoxy, lower alkylamino and the like.

The term "heteroaryl," alone or in combination, as used herein, means an aromatic system wherein at least one carbon atom is replaced by a heteroatom selected from N, S and O. A heteroaryl can contain one or more rings, which may be attached together in a pendent manner or may be fused. In some embodiments, a heteroaryl has one, two or three rings. In one aspect, the heteroaryl has five to twelve ring atoms. The term "heteroaryl" encompasses heteroaromatic groups such as triazolyl, imidazolyl, pyrrolyl, pyrazolyl, tetrazolyl, pyridyl, pyrimidinyl, pyrazinyl, pyridazinyl, indolyl, furyl, benzofuryl, thienyl, benzothienyl, quinolyl, oxazolyl, oxadiazolyl, isoxazolyl, and the like. A "heteroaryl" group can have 1 to 4 substituents, such as lower alkyl, hydroxyl, halo, haloalkyl, nitro, cyano, alkoxy, lower alkylamino and the like.

It is understood that substituents and substitution patterns on the compounds of the invention can be selected by one of ordinary skill in the art to provide compounds that are chemically stable and that can be readily synthesized by techniques known in the art, as well as those methods set forth below. In general, the term "substituted," whether preceded by the term "optionally" or not, means that one or more hydrogens of the designated moiety are replaced with a suitable substituent. Unless otherwise indicated, an "optionally substituted group" can have a suitable substituent at each substitutable position of the group and, when more than one position in any given structure may be substituted with more than one substituent selected from a specified group, the substituent can be either the same or different at every position. Alternatively, an "optionally substituted group" can be unsubstituted.

Combinations of substituents envisioned by this invention are preferably those that result in the formation of stable or chemically feasible compounds. If a substituent is itself substituted with more than one group, it is understood that these multiple groups can be on the same carbon atom or on different carbon atoms, as long as a stable structure results. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted group" are independently halogen; haloalkyl; —(CH$_2$)$_{0-4}$R$^\circ$, —(CH$_2$)$_{0-4}$OR$^\circ$; —O(CH$_2$)$_{0-4}$R$^\circ$, —O—(CH$_2$)$_{0-4}$C(O)OR$^\circ$, —(CH$_2$)$_{0-4}$CH(OR$^\circ$)$_2$; —(CH$_2$)$_{0-4}$SR$^\circ$: —(CH$_2$)$_{0-4}$Ph, which may be substituted with R$^\circ$; —(CH$_2$)$_{0-4}$O(CH$_2$)$_{0-4}$Ph which may be substituted with R$^\circ$; —CH=CHPh, which may be substituted with R$^\circ$; —(CH$_2$)$_{0-4}$O(CH$_2$)$_{0-4}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$C(S)R$^\circ$; —(CH$_2$)$_{0-4}$N(R$^\circ$)C(O)NR$^\circ$$_2$; —N(R$^\circ$C(S)NR$^\circ$$_2$;

—$(CH_2)_{0-4}N(R^\circ)C(O)OR^\circ$; —$N(R^\circ)N(R^\circ C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$—, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ_2$; $SiR^\circ_3$; —$(C_{1-4}$ straight or branched)alkylene)O—$N(R^\circ_2$; or —$(C_{1-4}$ straight or branched)alkylene)C(O)O—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, and sulfur, or, notwithstanding the definition above, two independent occurrences of $R^\circ$, taken together with their intervening atom(s), form a 3-12-membered saturated, partially unsaturated, or aryl monocyclic or bicyclic ring having 0-4 heteroatoms independently selected from nitrogen, oxygen, and sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(haloR$^\bullet$), —$(CH_2)_{0-2}OH$, —$(CH_2)_{0-2}OR^\bullet$, —$(CH_2)_{0-2}CH(OR^\bullet)_2$; —O(haloR$^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4}$ straight or branched alkylene)$C(O)OR^\bullet$, or —SSR$^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur. Suitable divalent substituents on a saturated carbon atom of $R^\circ$ include =O and =S.

Suitable divalent substituents on a saturated carbon atom of an "optionally substituted group" include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, and —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —$NH_2$, —NHR$^\bullet$, —NR$^\bullet_2$, and —$NO_2$, wherein each R$^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted group" include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, and —N(R$^\dagger$)S(O)$_2$R$^\dagger$; wherein each R$^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R$^\dagger$, taken together with their intervening atom(s) form an unsubstituted 3-12-membered saturated, partially unsaturated, or aryl monocyclic or bicyclic ring having 0-4 heteroatoms independently selected from nitrogen, oxygen, and sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —$NH_2$, —NHR$^\bullet$, —NR$^\bullet_2$, or —$NO_2$, wherein each R$^\bullet$ is unsubstituted or where preceded by "halo" is substituted only with one or more halogens, and is independently $C_{1-4}$ aliphatic, —$CH_2Ph$, —$O(CH_2)_{0-3}Ph$, or a 5-6-membered saturated, partially unsaturated, or aryl ring having 0-4 heteroatoms independently selected from nitrogen, oxygen, and sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, the relevant teachings of which are incorporated herein by reference in their entirety. Pharmaceutically acceptable salts of the compounds of this invention include salts derived from suitable inorganic and organic acids and bases that are compatible with the treatment of subjects.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable acid addition salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodate, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

In some embodiments, exemplary inorganic acids which form suitable salts include, but are not limited thereto, hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms.

In some embodiments, acid addition salts of the compounds of Formula (I) are most suitably formed from pharmaceutically acceptable acids, and include, for example, those formed with inorganic acids, e.g., hydrochloric, sulfuric or phosphoric acids and organic acids e.g. succinic, maleic, acetic or fumaric acid.

Other non-pharmaceutically acceptable salts, e.g., oxalates can be used, for example, in the isolation of compounds of Formula (I) for laboratory use, or for subsequent conversion to a pharmaceutically acceptable acid addition salt. Also included within the scope of the invention are base addition salts (such as sodium, potassium and ammonium salts), solvates and hydrates of compounds of the invention. The conversion of a given compound salt to a desired compound salt is achieved by applying standard techniques, well known to one skilled in the art.

A "pharmaceutically acceptable basic addition salt" is any non-toxic organic or inorganic base addition salt of the acid compounds represented by Formula (I), or any of its intermediates. Illustrative inorganic bases which form suitable salts include, but are not limited thereto, lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality, if any, elsewhere in the molecule is not hydrolyzed. The selection criteria for the appropriate salt will be known to one skilled in the art.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds produced by the replacement of a hydrogen with deuterium or tritium, or of a carbon with a $^{13}C$- or $^{14}C$-enriched carbon are within the scope of this invention. Such compounds are useful, for example, as analytical tools, as probes in biological assays, or as therapeutic agents in accordance with the present invention.

The term "stereoisomers" is a general term for all isomers of an individual molecule that differ only in the orientation of their atoms in space. It includes mirror image isomers (enantiomers), geometric (cis/trans) isomers and isomers of compounds with more than one chiral center that are not mirror images of one another (diastereomers).

The term "subject", as used herein, means an animal. In some embodiments, the animal is a mammal. In certain embodiments, the subject is a veterinary subject (i.e., a non-human mammal subject), such as a pig or a horse. In some embodiments, the subject is a dog. In other embodiments, the subject is a human.

The term "treat" or "treating" means to alleviate one or more symptoms, to eliminate the causation of one or more symptoms, either on a temporary or permanent basis, or to prevent or delay the onset of one or more symptoms associated with a disorder or condition.

The term "epilepsy" includes idiopathic epilepsy, cryptogenic epilepsy and symptomatic epilepsy. Idiopathic epilepsy means there is no apparent cause. Idiopathic epilepsy could be due to genetic tendency. Cryptogenic epilepsy occurs when the cause for a person's epilepsy has not yet been found, despite investigation. Symptomatic epilepsy is epilepsy with a known cause. Causes of symptomatic epilepsy can include a head injury, an infection like meningitis, a stroke, a scar or a tumor. In one embodiment, the subject being treated suffers from cryptogenic or idiopathic epilepsy. In another embodiment, the subject being treated suffers from symptomatic epilepsy. In one aspect, the symptomatic epilepsy is not a result of a brain injury.

The term "therapeutically effective amount" or "effective amount" are used interchangeably and mean an amount of a compound that is effective in treating or lessening the severity of one or more symptoms of a disorder or condition. In the case of epilepsy, a therapeutically effective amount is an amount that promotes a decrease in frequency and/or severity of epileptic seizures.

As used herein, "treating epilepsy" means treating a subject with a diagnosis of epileptic seizures. Treating epilepsy can mean, e.g., one or more of the following: reducing the occurrence of epileptic seizures, reducing the severity and/or duration of epileptic seizures, including partial, generalized, convulsive and non-convulsive seizures, and reducing the severity and/or duration of seizures selected from tonic-clonic, tonic, clonic, myoclonic, absence, and atonic seizures. All types involve loss of consciousness and typically happen without warning.

Tonic-clonic seizures occur with a contraction of the limbs followed by their extension along with arching of the back which lasts 10-30 seconds (the tonic phase). Tonic seizures produce constant contractions of the muscles. In clonic seizures, there is shaking of the limbs in unison. After the shaking has stopped, it may take 10-30 minutes for the subject to return to baseline. Myoclonic seizures involve spasms of muscles in either a few areas or all over. Absence seizures can be subtle with only a slight turn of the head or eye blinking. The subject does not lose balance and returns to normal right after it ends. Atonic seizures involve the loss of muscle activity for greater than one second, which typically occurs on both sides of the body.

Treating epilepsy can also involve reducing an abnormal and excessive firing of excitory neurons during a seizure, thus reducing the severity and scope of a seizure. Treating epilepsy can also result in resolution of the disease, meaning that the subject has not experienced a seizure during a 10-year period.

The term "treating epilepsy" also includes the treatment of epilepsy syndromes. The term "epilepsy syndrome" refers to a set of features that are present in the subject having unprovoked seizures. For example, features can include the age that seizure begin, the seizure types, and EEG findings. Diagnosis of a syndrome can inform selection of medication treatment. Exemplary syndromes are benign rolandic epilepsy, childhood absence epilepsy, juvenile myoclonic epilepsy, Lennox-Gastaut syndrome, and West syndrome.

When introducing elements disclosed herein, the articles "a," "an," "the," and "said" are intended to mean that there are one or more of the elements. The terms "comprising," "having" and "including" are intended to be open-ended and mean that there may be additional elements other than the listed elements.

Exemplary Embodiments

A first embodiment is a method of treating epilepsy in a subject in need thereof, the method comprising administering to the subject an effective amount of a compound represented by structural Formula (I):

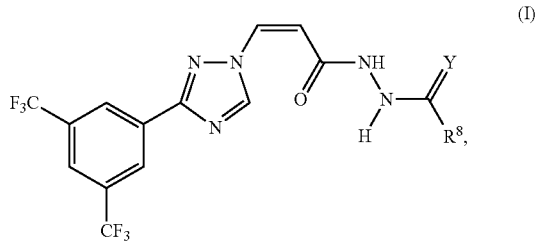

or a pharmaceutically acceptable salt thereof, wherein:
Y is O or S;
$R^8$ is selected from —N($R^9$)—($C_3$-$C_6$ cycloalkyl), —$C_3$-$C_6$ alkyl, —($C_0$-$C_1$ alkylene)-heterocyclyl, and —($C_0$-$C_1$ alkylene)-heteroaryl;
$R^9$ is selected from hydrogen and $C_1$-$C_4$ alkyl; wherein:
any alkyl or alkylene portion of any $R^8$ is optionally and independently substituted with one or more substituents selected from oxo and —N($R^7$)$_2$, wherein each $R^7$ is independently selected from hydrogen and $C_1$-$C_4$ alkyl;
any heterocyclyl portion of $R^8$ comprises at least one nitrogen atom in a ring, and is optionally substituted with one or more substituents selected from $C_1$-$C_4$ alkyl and oxo; and any heteroaryl portion of $R^8$ comprises at least one nitrogen atom in a ring and is optionally substituted with one or more $C_1$-$C_4$ alkyl.

In a second embodiment, for the compound of Formula (I), Y is O.

In a first aspect of the first or second embodiment, $R^8$ is selected from —N($R^9$)—($C_3$-$C_6$ cycloalkyl), —$C_3$-$C_6$ alkyl, —($C_0$-$C_1$ alkylene)-heterocyclyl, and —($C_0$-$C_1$ alkylene)-heteroaryl, wherein any alkyl or alkylene portion of $R^8$ is optionally substituted with —N($R^7$)$_2$, wherein each $R^7$ and $R^9$ is independently selected from hydrogen and $C_1$-$C_4$ alkyl; any heterocyclyl, and heteroaryl portion of $R^8$ comprises at least one nitrogen atom in a ring; and any heterocyclyl, and heteroaryl portion of $R^8$ is optionally substituted with $C_1$-$C_4$ alkyl.

In a second aspect of the first or second embodiment, $R^8$ is selected from —C(CH$_3$)$_3$, —CH(NH$_2$)—CH(CH$_3$)$_2$, —NH-cyclopropyl, —(CH$_2$)$_{0-1}$-pyrazinyl, piperidinyl, N-methylpiperidinyl, —CH$_2$-morpholin-4-yl, and methylpyrazolyl.

In a third aspect of the first or second embodiment, $R^8$ is selected from —C(CH$_3$)$_3$, —CH(NH$_2$)—H(CH$_3$)$_2$, —NH-cyclopropyl, —(CH$_2$)$_{0-1}$-pyrazin-2-yl, piperidin-3-yl, —CH$_2$-morpholin-4-yl, and 5-methyl-1-H-pyrazol-4-yl.

In a fourth aspect of the first or second embodiment, $R^8$ is selected from —C(CH$_3$)$_3$, —NH-cyclopropyl, —CH$_2$-pyrazin-2-yl, -pyrazin-2-yl, —CH$_2$-morpholin-4-yl, and 5-methyl-1-H-pyrazol-4-yl.

In a fifth aspect of the first or second embodiment, $R^8$ is —($C_0$-$C_1$alkylene)-heterocyclyl.

In an sixth aspect of the first or second embodiment, $R^8$ is —($C_0$-$C_1$ alkylene)-heterocyclyl, wherein the heterocyclyl is selected from pyrazinyl, piperidinyl, morpholinyl, and pyrazolyl.

In a seventh aspect of the first or second embodiment, $R^8$ is —($C_0$-$C_1$ alkylene)-heterocyclyl, wherein the heterocyclyl is morpholinyl.

In a eighth aspect of the first or second embodiment, $R^8$ is —($C_1$alkylene)-heterocyclyl.

In a ninth aspect of the first or second embodiment, $R^8$ is —($C_1$alkylene)-morpholinyl.

In a twelfth aspect of the first or second embodiment, $R^8$ is selected from —C(CH$_3$)$_3$, —CH(NH$_2$)—CH(CH$_3$)$_2$, —NH-cyclopropyl, —(CH$_2$)$_{0-1}$-pyrazin-2-yl, piperidin-3-yl, —CH$_2$-morpholin-4-yl, and 5-methyl-1-H-pyrazol-4-yl.

In a tenth aspect of the first or second embodiment, $R^8$ is selected from —C(CH$_3$)$_3$, —NH-cyclopropyl, —CH$_2$-pyrazin-2-yl, -pyrazin-2-yl, —CH$_2$-morpholin-4-yl, and 5-methyl-1-H-pyrazol-4-yl.

In a eleventh aspect of the first or second embodiment, the compounds of Formula (I) for use in the claimed method is selected from any one of compounds E-1 to E-15 of Table 1 or a pharmaceutically acceptable salt thereof.

In a twelfth aspect of the first or second embodiment, the compound use in the claimed method is

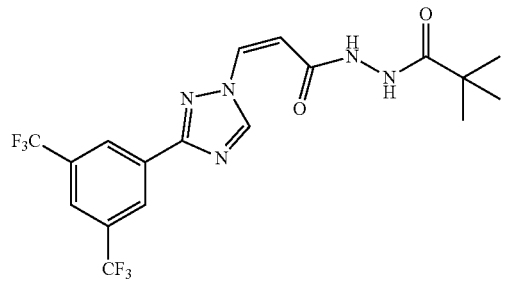 [SMILES: CC(C)(C)C(=O)NNC(=O)/C=C\n1cnc(-c2cc(C(F)(F)F)cc(C(F)(F)F)c2)n1]

or a pharmaceutically acceptable salt thereof.

In a thirteenth aspect of the first or second embodiment or any aspect thereof, the epilepsy can be characterized as having unprovoked partial or generalized seizures. These seizures can be convulsive or non-convulsive. There are six main types of seizures that are categorized by their type and duration: tonic-clonic, tonic, clonic, myoclonic, absence, and atonic seizures.

In a fourteenth aspect of the first or second embodiment or any aspect thereof, the seizure is partial or generalized, convulsive or non-convulsive, and selected from tonic-clonic, tonic, clonic, myoclonic, absence, and atonic seizures.

In a fifteenth aspect of the first or second embodiment or any aspect thereof, the seizure is partial and convulsive.

In a sixteenth aspect of the first or second embodiment or any aspect thereof, the epilepsy is idiopathic epilepsy.

In a seventeenth aspect of the first or second embodiment or any aspect thereof, the epilepsy is cryptogenic epilepsy.

In a eighteenth aspect of the first or second embodiment of any aspect thereof, the epilepsy is symptomatic epilepsy.

In a nineteenth aspect of the first or second embodiment or any thereof, the epilepsy is symptomatic epilepsy caused by a stroke, a tumor or an infection.

Methods of making the compounds of Table 1 and compounds of Formula (I) wherein Y is O or S, and $R^8$ is selected from optionally substituted —$N(R^9)$—($C_3$-$C_6$ cycloalkyl), —$C_3$-$C_6$ alkyl, —($C_0$-$C_1$ alkylene)-heterocyclyl, and —($C_0$-$C_1$ alkylene)-heteroaryl and $R^9$ is selected from hydrogen and $C_3$-$C_4$ alkyl are disclosed, for example, in U.S. Pat. No. 9,096,543, the entire contents of which are incorporated herein by reference.

TABLE 1

Exemplary Compounds

| Compound | Structure | Name |
|---|---|---|
| E-1 | 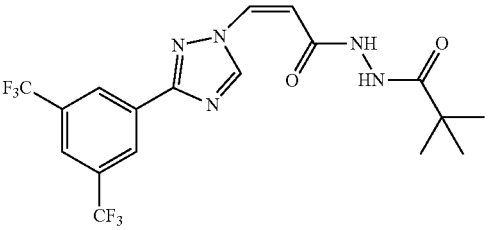 | (Z)-3-(3-(3,5-bis(trifluoromethyl)phenyl)-1H-1,2,4-triazol-1-yl)-N'-pivaloylacrylohydrazide |
| E-2 | 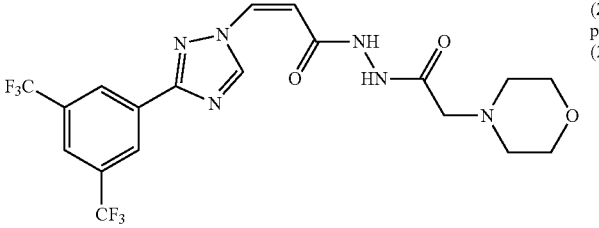 | (Z)-3-(3-(3,5-bis(trifluoromethyl)phenyl)-1H-1,2,4-triazol-1-yl)-N'-(2-morpholinoacetyl)acrylohydrazide |
| E-3 | 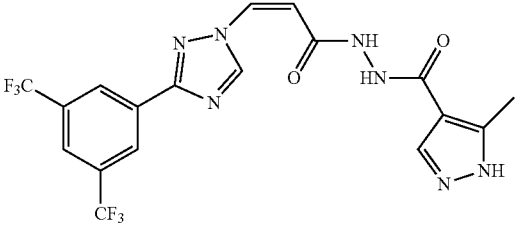 [SMILES: Cc1[nH]ncc1C(=O)NNC(=O)/C=C\n1cnc(-c2cc(C(F)(F)F)cc(C(F)(F)F)c2)n1] | (Z)-N'-(3-(3-(3,5-bis(trifluoromethyl)phenyl)-1H-1,2,4-triazol-1-yl)acryloyl)-5-methyl-1H-pyrazole-4-carbohydrazide |
| E-4 | 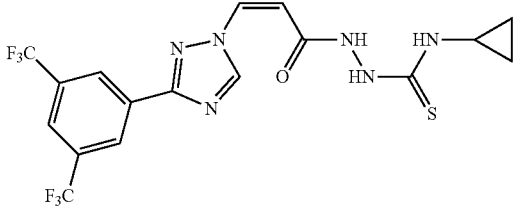 [SMILES: O=C(/C=C\n1cnc(-c2cc(C(F)(F)F)cc(C(F)(F)F)c2)n1)NNC(=S)NC1CC1] | (Z)-2-(3-(3-(3,5-bis(trifluoromethyl)phenyl)-1H-1,2,4-triazol-1-yl)acryloyl)-N-cyclopropylhydrazine carbothioamide |
| E-5 | 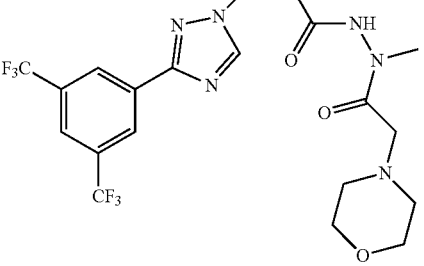 | (Z)-3-(3-(3,5-bis(trifluoromethyl)phenyl)-1H-1,2,4-triazol-1-yl)-N'-methyl-N'-(2-morpholinoacetyl)acrylohydrazide |

TABLE 1-continued

Exemplary Compounds

| Compound | Structure | Name |
|---|---|---|
| E-6 | 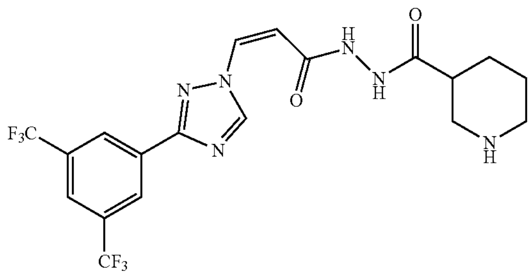 [SMILES: O=C(/C=C\n1cnc(-c2cc(C(F)(F)F)cc(C(F)(F)F)c2)n1)NNC(=O)C1CCCNC1] | (Z)-N'-(3-(3-(3,5-bis(trifluoromethyl)phenyl)-1H-1,2,4-triazol-1-yl)acryloyl)piperidine-3-carbohydrazide |
| E-7 | 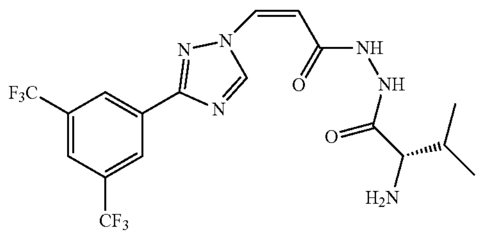 [SMILES: CC(C)[C@H](N)C(=O)NNC(=O)/C=C\n1cnc(-c2cc(C(F)(F)F)cc(C(F)(F)F)c2)n1] | (S,Z)-2-amino-N'-(3-(3-(3,5-bis(trifluoromethyl)phenyl)-1H-1,2,4-triazol-1-yl)acryloyl)-3-methylbutanehydrazide 2,2,2,-trifluoroacetate |
| E-8 | 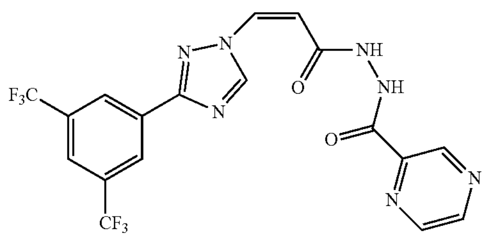 [SMILES: O=C(/C=C\n1cnc(-c2cc(C(F)(F)F)cc(C(F)(F)F)c2)n1)NNC(=O)c1cnccn1] | (Z)-N'-(3-(3-(3,5-bis(trifluoromethyl)phenyl)-1H-1,2,4-triazol-1-yl)acryloyl)pyrazine-2-carbohydrazide |
| E-9 | 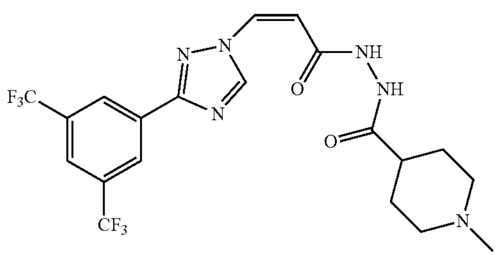 [SMILES: CN1CCC(C(=O)NNC(=O)/C=C\n2cnc(-c3cc(C(F)(F)F)cc(C(F)(F)F)c3)n2)CC1] | (Z)-N'-(3-(3-(3,5-bis(trifluoromethyl)phenyl)-1H-1,2,4-triazol-1-yl)acryloyl)-1-methylpiperidine-4-carbohydrazide |
| E-10 | 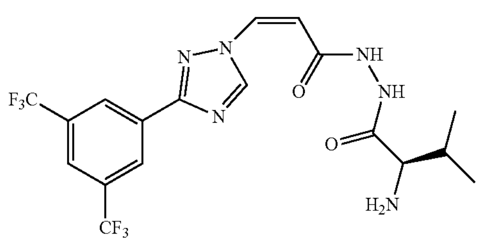 [SMILES: CC(C)[C@@H](N)C(=O)NNC(=O)/C=C\n1cnc(-c2cc(C(F)(F)F)cc(C(F)(F)F)c2)n1] | (R,Z)-2-amino-N'-(3-(3-(3,5-bis(trifluoromethyl)phenyl)-1H-1,2,4-triazol-1-yl)acryloyl)-3-methylbutanehydrazide 2,2,2,-trifluoroacetate |
| E-11 | 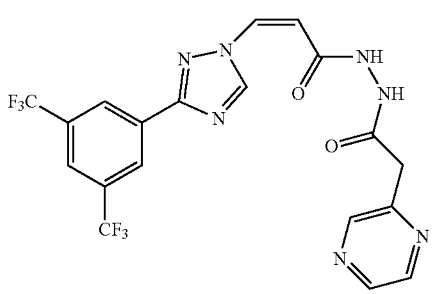 [SMILES: O=C(/C=C\n1cnc(-c2cc(C(F)(F)F)cc(C(F)(F)F)c2)n1)NNC(=O)Cc1cnccn1] | (Z)-3-(3-(3,5-bis(trifluoromethyl)phenyl)-1H-1,2,4-triazol-1-yl)-N'-(2-(pyrazin-2-yl)acetyl)acrylohydrazide |

TABLE 1-continued

Exemplary Compounds

| Compound | Structure | Name |
|---|---|---|
| E-12 | 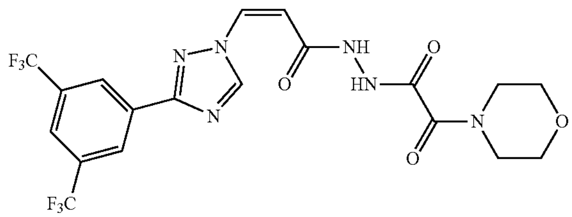 [SMILES: O=C(/C=C\n1cnc(-c2cc(C(F)(F)F)cc(C(F)(F)F)c2)n1)NNC(=O)C(=O)N1CCOCC1] | (Z)-3-(3-(3,5-bis(trifluoromethyl)phenyl)-1H-1,2,4-triazol-1-yl)-N'-(2-morpholino-2-oxoacetyl)acrylohydrazide |
| E-13 | 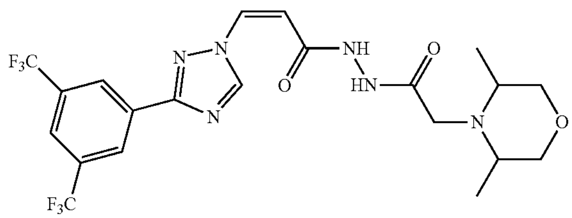 [SMILES: CC1COCC(C)N1CC(=O)NNC(=O)/C=C\n1cnc(-c2cc(C(F)(F)F)cc(C(F)(F)F)c2)n1] | (Z)-3-(3-(3,5-bis(trifluoromethyl)phenyl)-1H-1,2,4-triazol-1-yl)-N'-(2-(3,5-dimethylmorpholino)acetyl)acrylohydrazide |
| E-14 | 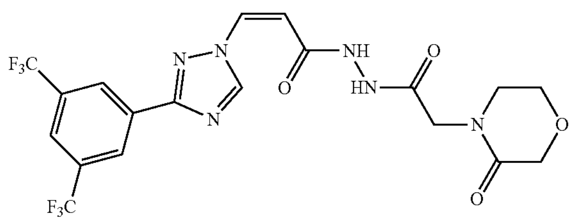 [SMILES: O=C(/C=C\n1cnc(-c2cc(C(F)(F)F)cc(C(F)(F)F)c2)n1)NNC(=O)CN1CCOCC1=O] | (Z)-3-(3-(3,5-bis(trifluoromethyl)phenyl)-1H-1,2,4-triazol-1-yl)-N'-(2-(3-oxomorpholino)acetyl)acrylohydrazide |
| E-15 | 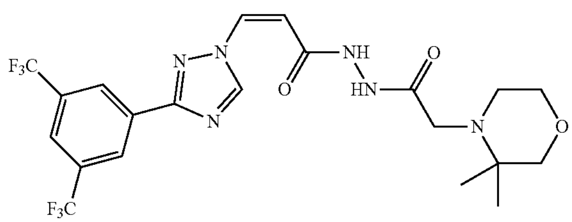 [SMILES: CC1(C)COCCN1CC(=O)NNC(=O)/C=C\n1cnc(-c2cc(C(F)(F)F)cc(C(F)(F)F)c2)n1] | (Z)-3-(3-(3,5-bis(trifluoromethyl)phenyl)-1H-1,2,4-triazol-1-yl)-N'-(2-(3,3-dimethylmorpholino)acetyl)acrylohydrazide |

In some embodiments, the compound is selected from

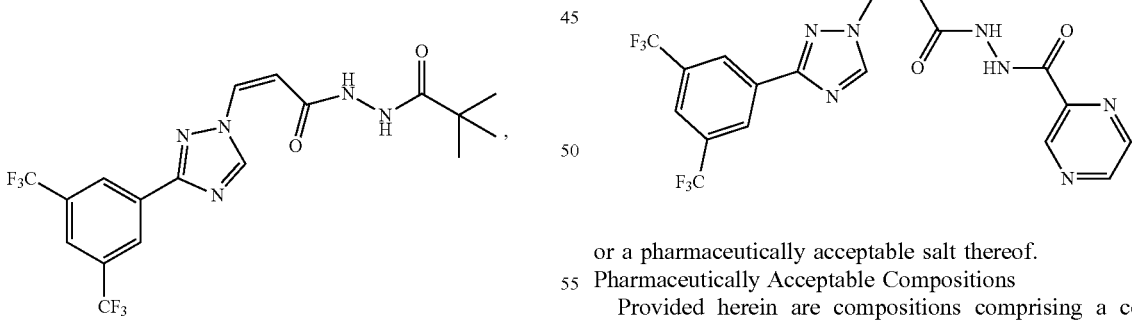

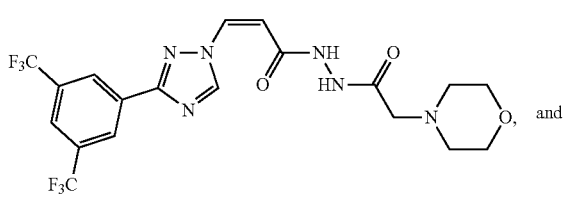

or a pharmaceutically acceptable salt thereof.

Pharmaceutically Acceptable Compositions

Provided herein are compositions comprising a compound of this invention or a pharmaceutically acceptable salt thereof and a pharmaceutically acceptable carrier, adjuvant, or vehicle. The amount of compound in compositions of this invention is such that is effective to measurably inhibit CRM1 in a biological sample or in a subject. In certain embodiments, a composition of this invention is formulated for administration to a subject in need of such composition.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Other pharmaceutically acceptable carriers, adjuvants or vehicles include water, saline and dimethylsulfoxide, as well as other hydrophobic or hydrophilic solvents.

Compositions of the present invention may be administered orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or intraperitonally. Preferably, the compounds and compositions described herein are administered orally or parenterally.

The term "parenteral," as used herein, includes subcutaneous, intravenous, intramuscular, intraocular, intravitreal, intra-articular, intra-synovial, intrasternal, intrathecal, intrahepatic, intraperitoneal, intralesional and intracranial injection or infusion techniques. Preferably, the compositions are administered orally, subcutaneously, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A compound disclosed herein can also be in micro-encapsulated form.

The amount of a compound of the present invention that may be combined with the carrier materials to produce a composition in a single dosage form will vary depending upon the subject being treated and the particular mode of administration. In one embodiment, provided compositions should be formulated so that a dosage of between about 0.01-about 100 mg/kg body weight/day of the compound can be administered to a subject receiving these compositions. In another embodiment, the dosage is from about 0.5 to about 100 mg/kg of body weight, or between about 1 mg and about 1000 mg/dose, about every 4 to 120 hours, or according to the requirements of the particular drug. Typically, the pharmaceutical compositions of this invention will be administered from about 1 to about 6 times per day.

In some embodiments, the compound is formulated for oral administration at a dosage of approximately 5 mg/kg to approximately 10 mg/kg, preferably at a dosage of approximately 7.5 mg/kg.

In some embodiments, the compound is formulated for topical administration at a concentration of approximately 0.3 μM to approximately 10 μM.

It should also be understood that a specific dosage and treatment regimen for any particular subject will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

Methods

Specific proteins and RNAs are carried into and out of the nucleus by specialized transport molecules, which are classified as importins if they transport molecules into the nucleus, and exportins if they transport molecules out of the nucleus. Proteins that are transported into or out of the nucleus contain nuclear import/localization (NLS) or export (NES) sequences that allow them to interact with the relevant transporters. Chromosomal Region Maintenance 1 (CRM1), which is also called exportin-1 or Xpo1, is a major exportin. Inhibition of CRM1 blocks the exodus of proteins and/or growth regulators such as p53, c-Abl, p21, p27, pRB, BRCA1, IkB, ICp27, E2F4, KLF5, YAP1, ZAP, KLF5, HDAC4, HDAC5 or forkhead proteins (e.g. FOXO3a) from the nucleus that are associated with gene expression, cell proliferation, angiogenesis, neurological disorders, and epigenetics.

Compounds and compositions described herein are generally useful for the inhibition of CRM1 and are therefore useful for treating one or more disorders associated with activity of CRM1, such as epilepsy. Thus, in certain embodiments, the present invention provides a method for treating epilepsy comprising the step of administering to a subject in need thereof a compound of the present invention, or pharmaceutically acceptable composition thereof. In some embodiments, the epilepsy is present in an epilepsy syndrome. The compounds and compositions described herein can also be administered to cells in culture, e.g. in vitro or ex vivo, or to a subject, e.g., in vivo, to treat, prevent, and/or diagnose a variety of epilepsy disorders, including those described herein below.

Another embodiment of the invention is a method for treating a epilepsy or an epilepsy syndrome disorder associated with CRM1 activity in a subject in need thereof, the method comprising administering to the subject in need thereof a therapeutically effective amount of a compound of Formula (I), or a pharmaceutically acceptable salt or composition thereof. In some embodiments, the epilepsy is present in an epilepsy syndrome.

The activity of a compound utilized in this invention as an inhibitor of CRM1 may be assayed in vitro, in vivo or in a cell line. Detailed conditions for assaying a compounds inhibitors of CRM1 are set forth in U.S. Pat. No. 9,096,543, and International Application Nos. PCT/US2011/027328; PCT/US2012/048368; PCT/US2012/048319; PCT/US2012/021406; and PCT/2014/04479, the entire contents of which are hereby incorporated by reference. The activity of many of the compounds described herein in assays designed to measure CRM1 inhibitory activity can also be found in U.S. Pat. No. 9,096,543, and International Application Nos. PCT/US2011/027328; PCT/US2012/048368; PCT/US2012/048319; PCT/US2012/021406; and PCT/2014/04479.

Compounds of the invention (the compounds represented by structural Formula (I), and pharmaceutically acceptable salts thereof, are also useful in the manufacture of a medicament for the treatment of epilepsy or an epilepsy syndrome disorder. Also provided herein are disclosed compounds and compositions for use in the treatment of epilepsy.

Combination Therapies

In some embodiments, a compound described herein is administered together with an additional "second" therapeutic agent or treatment. The choice of second therapeutic agent may be made from any agent that is typically used in a monotherapy to treat epilepsy. As used herein, the term "administered together" and related terms refers to the simultaneous or sequential administration of therapeutic agents in accordance with this invention. For example, a therapeutically effective amount of a compound of the present invention may be administered with a therapeutically effective amount of another therapeutic agent simultaneously or sequentially in separate unit dosage forms or together in a single unit dosage form. Accordingly, the present invention provides a single unit dosage form comprising a compound of the invention, an additional therapeutic agent, and a pharmaceutically acceptable carrier, adjuvant, or vehicle.

In one embodiment of the invention, where a second therapeutic agent is administered to a subject, the therapeutically effective amount of the compound of this invention is less than its therapeutically effective amount would be where the second therapeutic agent is not administered. In another embodiment, the therapeutically effective amount of the second therapeutic agent is less than its therapeutically effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art. The additional agents may be administered separately, as part of a multiple dose regimen, from the compounds of this invention. Alternatively, those agents may be part of a single dosage form, mixed together with the compounds of this invention in a single composition.

The amount of both a compound of the invention and additional therapeutic agent (in those compositions which comprise an additional therapeutic agent as described above) that can be combined with the carrier materials to produce a single dosage form will vary depending upon the host treated and the particular mode of administration. Preferably, compositions of this invention should be formulated so that a dosage of between about 0.01-about 100 mg/kg body weight/day of a compound of the invention can be administered. In certain embodiments, a therapeutically effective amount of a compound described herein may be administered alone or in combination with therapeutically effective amounts of other compounds useful for treating epilepsy or epilepsy syndrome disorders.

Examples of antiseizure medications that can be used in combination with the compounds described herein include, but are not limited to, lamictal, Topamax, lamotrigine, klonopin, clonazepam, topiramate, valium, diazepam, dpeacon and depakene.

EXEMPLIFICATION

Example 1

Pilocarpine Model for the Study of Temporal Lobe Epilepsy (TLE)

A well-established pilocarpine model of temporal lobe epilepsy (TLE) that has been recently optimized for mice can be used (Mazzuferi et al., *Exp. Neurol.* 238:156-67). Status epilepticus (SE) can be initiated with a single 300 mg/kg intraperitoneal (i.p.) injection of pilocarpine in male NMRI mice, 30 min after N-methylscopolamine bromide administration (1 mg/kg; i.p.). Within 10 to 45 min after pilocarpine treatment, animals display generalized tonic-clonic seizures that progress to continuous convulsive activity, i.e. SE. To limit the duration of SE, mice can be injected with a bolus dose of diazepam (10 mg/kg; i.p.) after 3 h. The mice typically show spontaneous recurrent seizures within few days after SE and continue to display them throughout their lifetime.

mRNA measurement of Nrf2 downstream genes (heme oxygenase-1 [HO-1], quinone oxidoreductase 1 [NQO1], and microsomal glutathione S-transferase [mGST]) can be performed in micro-dissected hippocampi (for example, n=8) during the chronic phase of the pilocarpine mouse model, i.e., 8-10 weeks after pilocarpine-induced SE. The pilocarpine mice will be sacrificed after 4-day treatment with a disclosed compound (for example, 3 and 10 mg/kg (every other day) for a total of 2 doses). The same measurement will be performed in aged-matched control animals treated the same way with either vehicle (n=8) or a disclosed compound (n=8) to assess potential difference between epileptic and non-epileptic mice. Quantification can be performed with a Taqman real time quantitative polymerase chain reaction. In all experiments, mRNA levels are normalized to glyceraldehyde-3-phosphate dehydrogenase (GAPDH), which serves as the housekeeping gene.

A separate cohort of animals (for example, n=40) can then undergo continuous monitoring for spontaneous recurrent seizures during 28 consecutive days beginning 8-10 weeks following pilocarpine induced SE. The seizure monitoring can be performed by simultaneous recording of locomotor activity with a 3D accelerometer and video. This system allows for automated detection of behavioral seizures by analysis of the accelerometry signal. All behavioral seizures can be scored according to the Racine's protocol after detailed review of corresponding video clips by experienced technical personnel. Secondary generalized seizures, a Racine's score of 3-5, will be quantified and used for calculation of total seizure counts.

After establishing baseline seizure frequency (during 14 days of continuous monitoring), one group of pilocarpine mice can be treated for additional 14 days with a disclosed compound (for example, 10 mg/kg (every other day for 2-weeks)), (n=20) and vehicle (n=20) to assess treatment-related changes in seizure frequency. At the end of the treatment phase, the mice would be sacrificed for sampling of the hippocampus and extraction of RNA (one hemisphere) and histology (one hemisphere).

Example 2

Pilocarpine Model for the Study of Temporal Lobe Epilepsy (TLE)

Following the general procedure described in Example 1 and outlined in FIG. 1, Compound E1 of Table I was administered to mice during the treatment phase at 7.5 mg/kg per os every other day for the two weeks of treatment. Control mice were administered vehicle using the same regimen (Vehicle: 0.6% Plasdone PVT K29/32 puls 0.6% Poloxamer Pluronic F68 in water. A total of 24 mice were dosed with Compound E1 (also known as KPT-350). As can be seen in FIGS. 2-5, all treated mice had at least a 50% reduction in seizure activity and six had a 100% reduction. In addition, there was no change in body weight of the treated mice.

The teachings of all patents, published applications and references cited herein are incorporated by reference in their entirety.

While this invention has been shown and described with references to example embodiments thereof, it will be understood by those skilled in the art that various changes in form and details may be made therein without departing from the scope of the invention encompassed by the appended claims.

The invention claimed is:

1. A method of treating a subject suffering from epilepsy comprising administering to the subject a compound selected from:

| Cmpd No. | Compound Structure |
|---|---|
| E1 | 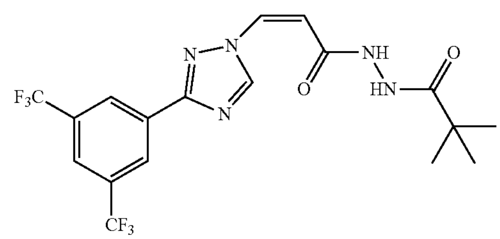 [SMILES: CC(C)(C)C(=O)NNC(=O)/C=C\n1cnc(-c2cc(C(F)(F)F)cc(C(F)(F)F)c2)n1] |
| E2 | 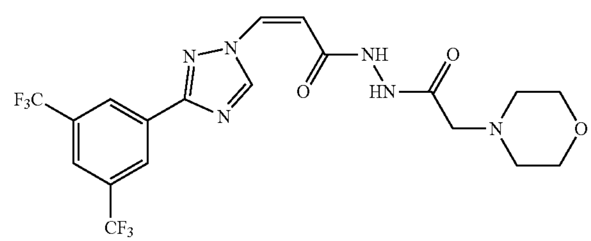 [SMILES: O=C(/C=C\n1cnc(-c2cc(C(F)(F)F)cc(C(F)(F)F)c2)n1)NNC(=O)CN1CCOCC1] |
| E3 | 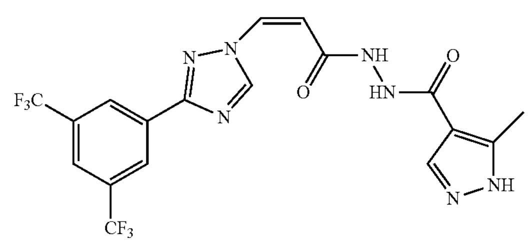 [SMILES: Cc1[nH]ncc1C(=O)NNC(=O)/C=C\n1cnc(-c2cc(C(F)(F)F)cc(C(F)(F)F)c2)n1] |
| E4 | 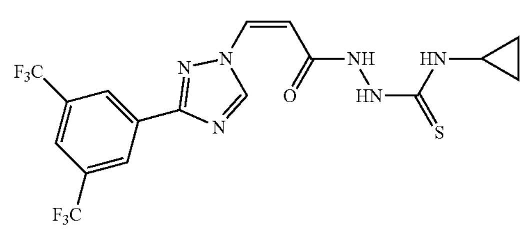 [SMILES: O=C(/C=C\n1cnc(-c2cc(C(F)(F)F)cc(C(F)(F)F)c2)n1)NNC(=S)NC1CC1] |

| Cmpd No. | Compound Structure |
|---|---|
| E5 | 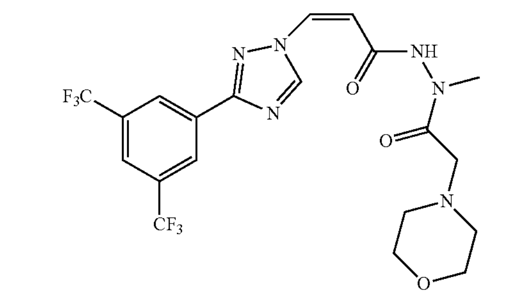 [SMILES: CN(NC(=O)/C=C\n1cnc(-c2cc(C(F)(F)F)cc(C(F)(F)F)c2)n1)C(=O)CN1CCOCC1] |
| E6 | 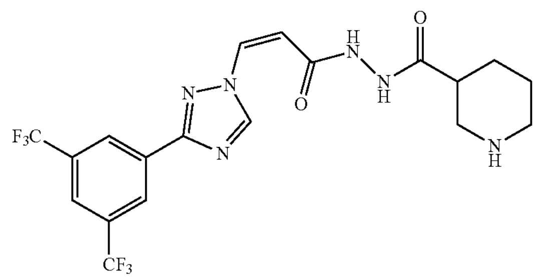 [SMILES: O=C(/C=C\n1cnc(-c2cc(C(F)(F)F)cc(C(F)(F)F)c2)n1)NNC(=O)C1CCCNC1] |
| E7 | 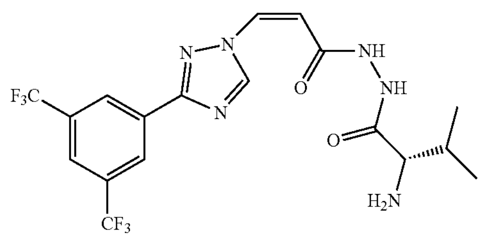 [SMILES: CC(C)[C@H](N)C(=O)NNC(=O)/C=C\n1cnc(-c2cc(C(F)(F)F)cc(C(F)(F)F)c2)n1] |
| E8 | 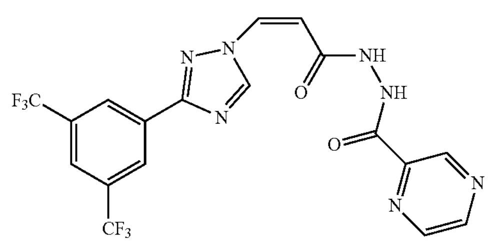 [SMILES: O=C(/C=C\n1cnc(-c2cc(C(F)(F)F)cc(C(F)(F)F)c2)n1)NNC(=O)c1cnccn1] |
| E9 | 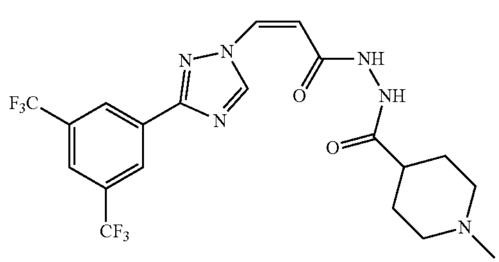 [SMILES: CN1CCC(C(=O)NNC(=O)/C=C\n2cnc(-c3cc(C(F)(F)F)cc(C(F)(F)F)c3)n2)CC1] |
| E10 | 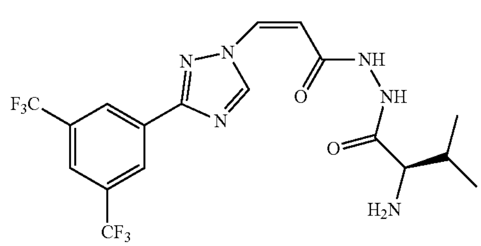 [SMILES: CC(C)[C@@H](N)C(=O)NNC(=O)/C=C\n1cnc(-c2cc(C(F)(F)F)cc(C(F)(F)F)c2)n1] |

-continued
| Cmpd No. | Compound Structure |
|---|---|
| E11 | 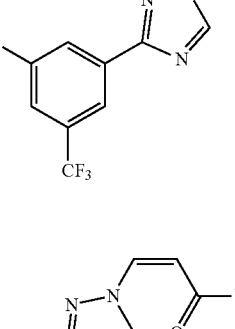 |
| E12 | 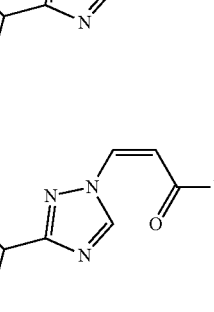 |
| E13 | 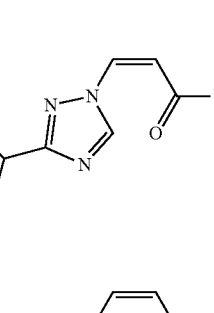 |
| E14 | 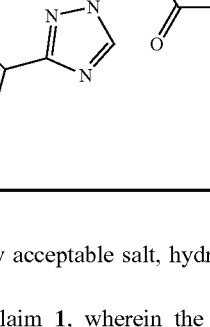 |
| E15 | 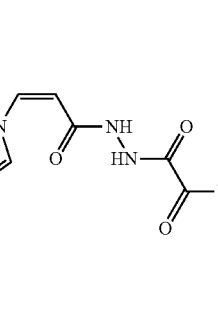 |
or a pharmaceutically acceptable salt, hydrate or solvate thereof.
2. The method of claim 1, wherein the compound is selected from
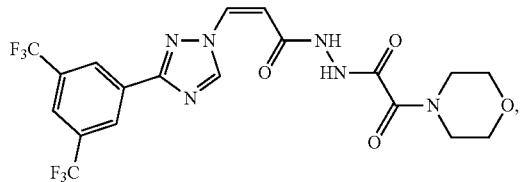
-continued
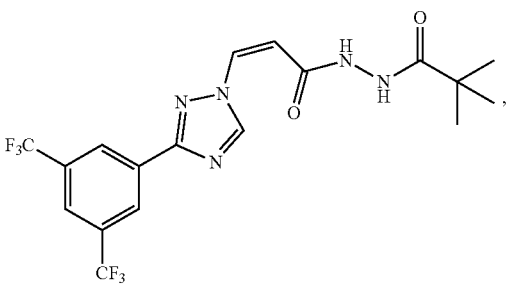

-continued
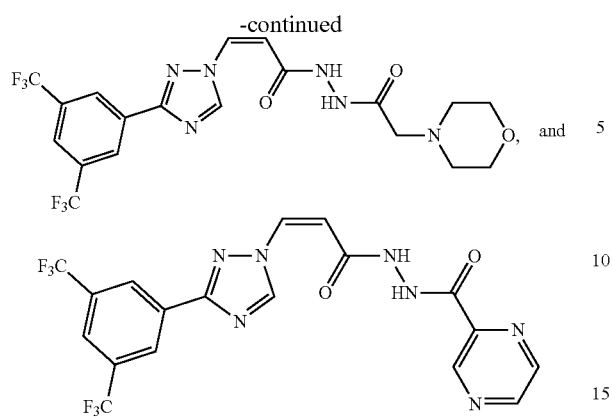
or a pharmaceutically acceptable salt, hydrate or solvate thereof.
3. The method of claim 2, wherein the compound is selected from
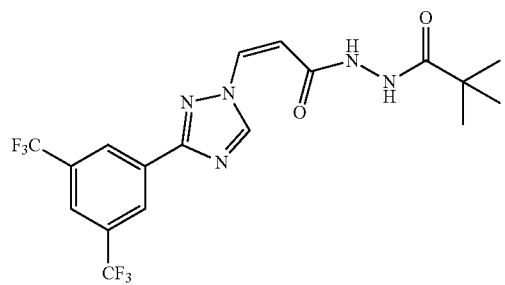 [SMILES: CC(C)(C)C(=O)NNC(=O)/C=C\n1cnc(-c2cc(C(F)(F)F)cc(C(F)(F)F)c2)n1]
or a pharmaceutically acceptable salt, hydrate or solvate thereof.
* * * * *